United States Patent
Mooney et al.

(10) Patent No.: US 10,628,047 B2
(45) Date of Patent: Apr. 21, 2020

(54) SYSTEM AND METHOD FOR MINIMIZING COMPUTATIONAL RESOURCES WHEN COPYING DATA FOR A WELL-BEING ASSESSMENT AND SCORING

(71) Applicant: Aetna Inc., Hartford, CT (US)

(72) Inventors: Kay D. Mooney, Durham, CT (US); Phillip J. Lerner, Avon, CT (US); Shawn Moore, Brooklyn Park, MN (US); Karen Ryan, Portland, CT (US); Amy Kruse, Avon, CT (US); Susan Salerno, Berlin, CT (US); Paul Mendelowitz, Park Ridge, NJ (US); Madhavi Vemireddy, New York, NY (US); Elena Koshkina, Collingswood, NJ (US); Derek Jackson, New York, NY (US); Amanda Widmaier, New York, NY (US); Pritesh Motipara, Montclair, NJ (US); Bridget K. McCabe, Staten Island, NY (US); Eileen McNeely, Belmont, MA (US); Tyler Vanderweele, Cambridge, MA (US)

(73) Assignee: Aetna Inc., Hartford, CT (US)

( * ) Notice: Subject to any disclaimer, the term of this patent is extended or adjusted under 35 U.S.C. 154(b) by 173 days.

(21) Appl. No.: 15/996,042

(22) Filed: Jun. 1, 2018

(65) Prior Publication Data
US 2018/0349027 A1 Dec. 6, 2018

Related U.S. Application Data
(60) Provisional application No. 62/514,448, filed on Jun. 2, 2017, provisional application No. 62/635,351, filed on Feb. 26, 2018.

(51) Int. Cl.
*G06F 16/00* (2019.01)
*G06F 3/06* (2006.01)
(Continued)

(52) U.S. Cl.
CPC .............. *G06F 3/061* (2013.01); *G06F 3/065* (2013.01); *G16H 50/30* (2018.01); *G16H 10/20* (2018.01); *G16H 10/65* (2018.01)

(58) Field of Classification Search
CPC .......... G06F 3/061; G06F 3/065; G06F 16/10; G06F 16/20; G16H 50/30; G16H 10/20; G16H 10/65
See application file for complete search history.

(56) References Cited

U.S. PATENT DOCUMENTS

| | | | |
|---|---|---|---|
| 6,802,810 B2 | 10/2004 | Ciarniello et al. | |
| 7,593,952 B2 * | 9/2009 | Soll | G06F 19/322 |

(Continued)

FOREIGN PATENT DOCUMENTS

| | | |
|---|---|---|
| CN | 102224503 A | 10/2011 |
| KR | 101439810 B1 | 9/2014 |

(Continued)

OTHER PUBLICATIONS

Bates et al., Big Data in Health Care: Using Analytics to Identify and Manage High-Risk and High-Cost Patients, Jul. 2014, 9 pages (Year: 2014).*

(Continued)

*Primary Examiner* — Noosha Arjomandi
(74) *Attorney, Agent, or Firm* — Leydig, Voit & Mayer LLP

(57) ABSTRACT

Disclosed is a method for minimizing computational resources when copying data. The method includes: receiving a first set of data from a first data source including portions (a) used to compute a well-being scoring, and (b)

(Continued)

not used to compute the well-being scoring; copying non-numerical data items included in the portion used to compute the well-being scoring to an aggregate data structure; and, for each numerical data item in the portion used to compute the well-being scoring: assigning a first data type to the numerical data item if it complies with the first data type, otherwise assigning a second data type to the numerical data item, where the first data type uses less bytes than the second data type, and copying, by the processor, the numerical data item to the aggregate data structure, wherein the well-being scoring is calculated for the member based on the aggregate data structure.

18 Claims, 8 Drawing Sheets

(51) Int. Cl.
    *G16H 50/30*    (2018.01)
    *G16H 10/20*    (2018.01)
    *G16H 10/65*    (2018.01)

(56) References Cited

U.S. PATENT DOCUMENTS

| | | | |
|---|---|---|---|
| 7,974,860 B1* | 7/2011 | Travis | G06Q 50/22 705/4 |
| 8,160,901 B2* | 4/2012 | Heywood | A61B 5/0002 705/3 |
| 8,620,591 B2 | 12/2013 | Wegerich | |
| 10,529,446 B2* | 1/2020 | Boland | G16H 80/00 |
| 2008/0015891 A1 | 1/2008 | Lee | |
| 2008/0015903 A1* | 1/2008 | Rodgers | G06Q 30/02 705/3 |
| 2009/0216558 A1* | 8/2009 | Reisman | G06F 19/328 705/3 |
| 2010/0004945 A1 | 1/2010 | Petratos et al. | |
| 2011/0060603 A1 | 3/2011 | Capelli et al. | |
| 2011/0119207 A1 | 5/2011 | Tong et al. | |
| 2011/0201902 A1 | 8/2011 | Shiga et al. | |
| 2013/0185097 A1* | 7/2013 | Saria | G06Q 10/00 705/3 |
| 2013/0289366 A1 | 10/2013 | Chua et al. | |
| 2013/0311197 A1 | 11/2013 | Hummer | |
| 2013/0332189 A1* | 12/2013 | Manning | G06Q 30/01 705/2 |
| 2014/0006039 A1 | 1/2014 | Khan et al. | |
| 2015/0213199 A1* | 7/2015 | Loeb | G16H 50/30 705/3 |
| 2016/0379511 A1* | 12/2016 | Dawson | G06F 3/04847 434/362 |
| 2017/0016896 A1* | 1/2017 | Eastman | G01N 33/564 |
| 2017/0109479 A1* | 4/2017 | Vemireddy | G06Q 10/00 |
| 2017/0193165 A1* | 7/2017 | Mandalika | G16H 50/30 |
| 2017/0262604 A1* | 9/2017 | Francois | G06F 19/3418 |
| 2018/0025116 A1* | 1/2018 | Carrington | G16H 50/30 705/3 |
| 2018/0035901 A1* | 2/2018 | Cronin | A61B 5/746 |
| 2018/0137247 A1* | 5/2018 | Bore | G16H 50/30 |
| 2018/0308569 A1* | 10/2018 | Luellen | G16H 20/10 |
| 2018/0349027 A1* | 12/2018 | Mooney | G06Q 10/00 |
| 2018/0358117 A1* | 12/2018 | Neagle | A61B 5/742 |
| 2018/0374174 A1* | 12/2018 | Clancy | G06Q 50/22 |
| 2019/0034593 A1* | 1/2019 | Bouman | G06Q 50/22 |
| 2019/0164650 A1* | 5/2019 | Schwartz | G06Q 40/08 |

FOREIGN PATENT DOCUMENTS

| | | |
|---|---|---|
| WO | WO 2008/008891 A2 | 1/2008 |
| WO | WO 2008/013553 A2 | 1/2008 |
| WO | WO 2012/090226 A2 | 7/2012 |

OTHER PUBLICATIONS

Brown et al., The Benefits of Being Present: Mindfulness and Its Role in Psychological Well-Being, 2003, 27 pages (Year: 2003).*

Roberge, et al. "The Health Utility Index: Measuring Health Differences in Ontario by Socioeconomic Status." Statistics Canada, Cat. No. 82-003, Health Reports 1995, vol. 7, No. 2, pp. 25-32 (1995).

Beevi, Haseena. "Health Status of Muslim Women in Kerala," Dept. of Economics, Sacred Heart College, Thevara, Ch. 1: Introduction, pp. 1-25 (Nov. 2012) (available at: http://shodhganga.inflibnet.ac.in/jspui/bitstream/10603/25806/9/09_chapter1.pdf).

CHCS (Center for Health Care Strategies, Inc.). "Predictive Modeling: A Guide for State Medicaid Purchasers" (Aug. 2009).

Population Health Alliance. "PHM Gloassary: I" (Nov. 8, 2015) (available at: http://www.populationhealthalliance.org/research/phm-glossary/i.html).

Wikipedia. "Radar Chart" (Feb. 29, 2016) (available at: https://web.archive.org/web/20160229054859/https://en.wikipedia.org/wiki/Radar_chart).

Minnesota Dept. of Health. "Radar Chart" (May 14, 2016) (available at: https://web.archive.org/web/20160514050348/http://www.health.state.mn.us/divs/opi/qi/toolbox/radar.html).

Visual Quest. "Health Care: Variations on a Theme—Profiles of a Malady" (Jul. 19, 2011) (available at: https://web.archive.org/web/20111225101530/http://www.visualquest.in:80/2011/07/health-care-variations-on-theme.html).

The Unstoppable Force. "Data Visualization Fail #3" (Dec. 21, 2010) (available at: http://theuforce.blogspot.com/2010/12/data-visualization-fail-3.html).

Brooker, et al. "Global Feasibility Assessment of Interrupting the Transmission of Soil-Transmitted Helminths: A Statistical Modelling Study," Lancet Infect. Dis. 2015, vol. 15, pp. 941-950 (Aug. 2015).

Jackson, et al. "It's All About Impactability! Optimizing Targeting for Care Management of Complex Patients," Community Care of North Carolina, Data Brief, Issue No. 4 (Nov. 2, 2015).

Gallup-Healthways. State of American Well-Being: 2014 State Well-Being Rankings (2014).

Ulanoff, Lance. "Amazon Knows What You Want Before You Buy It," Predictive Analytics Times (Jan. 27, 2014) (available at: https://www.predictiveanalyticsworld.com/patimes/amazon-knows-what-you-want-before-you-buy-it/3185/).

Hunter, James Davison. "Toward a Richer Understanding of the Moral Life: Three Disquieting Questions About the Contemporary Science of Morality," 4th Annual Jubilee Centre for Character and Virtues Conference, Oriel College, Oxford University (Jan. 7-9, 2016).

Shryack, et al. "The Structure of Virtue: An Empirical Investigation of the Dimensionality of the Virtues in Action Inventory of Strengths," Personality and Individual Differences, vol. 48, pp. 714-719 (2010).

Su, et al. "The Development and Validation of the Comprehensive Inventory of Thriving (CIT) and the Brief Inventory of Thriving (BIT)," Applied Psychology: Health Well-Being, vol. 6, pp. 251-279 (Jun. 2014).

Vanderweele, Tyler J. "On the Promotion of Human Flourishing," Proceedings of the National Academy of Sciences (PNAS), vol. 114, No. 31, pp. 8148-8156 (Aug. 1, 2017).

Mischel, et al. "Delay of Gratification in Children," Science, vol. 244, No. 4907, pp. 933-938 (May 26, 1989).

McNeely, et al. "Estimating the Health Consequences of Flight Attendant Work: Comparing Flight Attendant Health to the General Population in a Cross-Sectional Study," BMC Public Health, vol. 18 (Mar. 2018).

Peterson et al. "Character Strengths and Virtues: A Handbook and Classification," Oxford University Press (2004).

Pieper, Josef. "The Four Cardinal Virtues: Prudence, Justice, Fortitude, Temperance," University of Notre Dame Press (1966).

* cited by examiner

| IID | A | B | C | D | E | F | G | H | I | J |
|---|---|---|---|---|---|---|---|---|---|---|
| Member 1 | | | | | | | | | | |
| Member 2 | | | | | | | | | | |
| Member 3 | | | | | | | | | | |
| Member 4 | | | | | | | | | | |

FIG. 7

SYSTEM AND METHOD FOR MINIMIZING COMPUTATIONAL RESOURCES WHEN COPYING DATA FOR A WELL-BEING ASSESSMENT AND SCORING

CROSS-REFERENCE TO RELATED APPLICATIONS

This patent application claims priority of U.S. Provisional Patent Application Ser. No. 62/514,448 filed on Jun. 2, 2017 and also claims priority of U.S. Provisional Patent Application Ser. No. 62/635,351 filed on Feb. 26, 2018, both of which are hereby incorporated by reference in their entireties.

TECHNICAL FIELD

This disclosure relates generally to the field of health care management and, more specifically, to a system and method for minimizing computational resources when copying data for a well-being assessment and scoring.

BACKGROUND

The current healthcare environment suffers from the drawback of being "reactive," where a member of a health plan does not seek treatment until after an injury or illness has occurred. As such, the current healthcare environment has a narrow view of a member's overall heath.

SUMMARY

One embodiment provides a method and computer-readable medium for minimizing computational resources when copying data. The method includes: receiving, by a processor, a first set of data from a first data source, wherein the first set of data includes a portion of data used to compute a well-being scoring for a member and a portion of data not used to compute the well-being scoring for the member; copying, by the processor, non-numerical data items included in the portion of the data from the first set of data used to compute the well-being scoring to an aggregate data structure; and, for each numerical data item in the portion of the data from the first set of data used to compute the well-being scoring: assigning, by the processor, a first data type to the numerical data item if the numerical item complies with the first data type and assigning, by the processor, a second data type to the numerical data item if the numerical item does not comply with the first data type, wherein the first data type uses less bytes than the second data type to store the numerical data item, and copying, by the processor, the numerical data item having the assigned first or second data type to the aggregate data structure, wherein the well-being scoring is calculated for the member based on the aggregate data structure.

Another embodiment provides a computer system, comprising a memory storing instructions and a processor configured to execute the instructions to cause the computer system to: receive a first set of data from a first data source, wherein the first set of data includes a portion of data used to compute a well-being scoring for a member and a portion of data not used to compute the well-being scoring for the member; copy non-numerical data items included in the portion of the data from the first set of data used to compute the well-being scoring to an aggregate data structure; for each numerical data item in the portion of the data from the first set of data used to compute the well-being scoring: assign a first data type to the numerical data item if the numerical item complies with the first data type and assign a second data type to the numerical data item if the numerical item does not comply with the first data type, wherein the first data type uses less bytes than the second data type to store the numerical data item, and copy the numerical data item having the assigned first or second data type to the aggregate data structure; and generate the well-being scoring for the member based on the aggregate data structure.

BRIEF DESCRIPTION OF THE DRAWINGS

FIG. 7 is an example of a table of filtered data output by a data filtering engine and used by a well-being scoring calculation engine to compute a well-being scoring, according to one embodiment.

DETAILED DESCRIPTION

Figure 1:
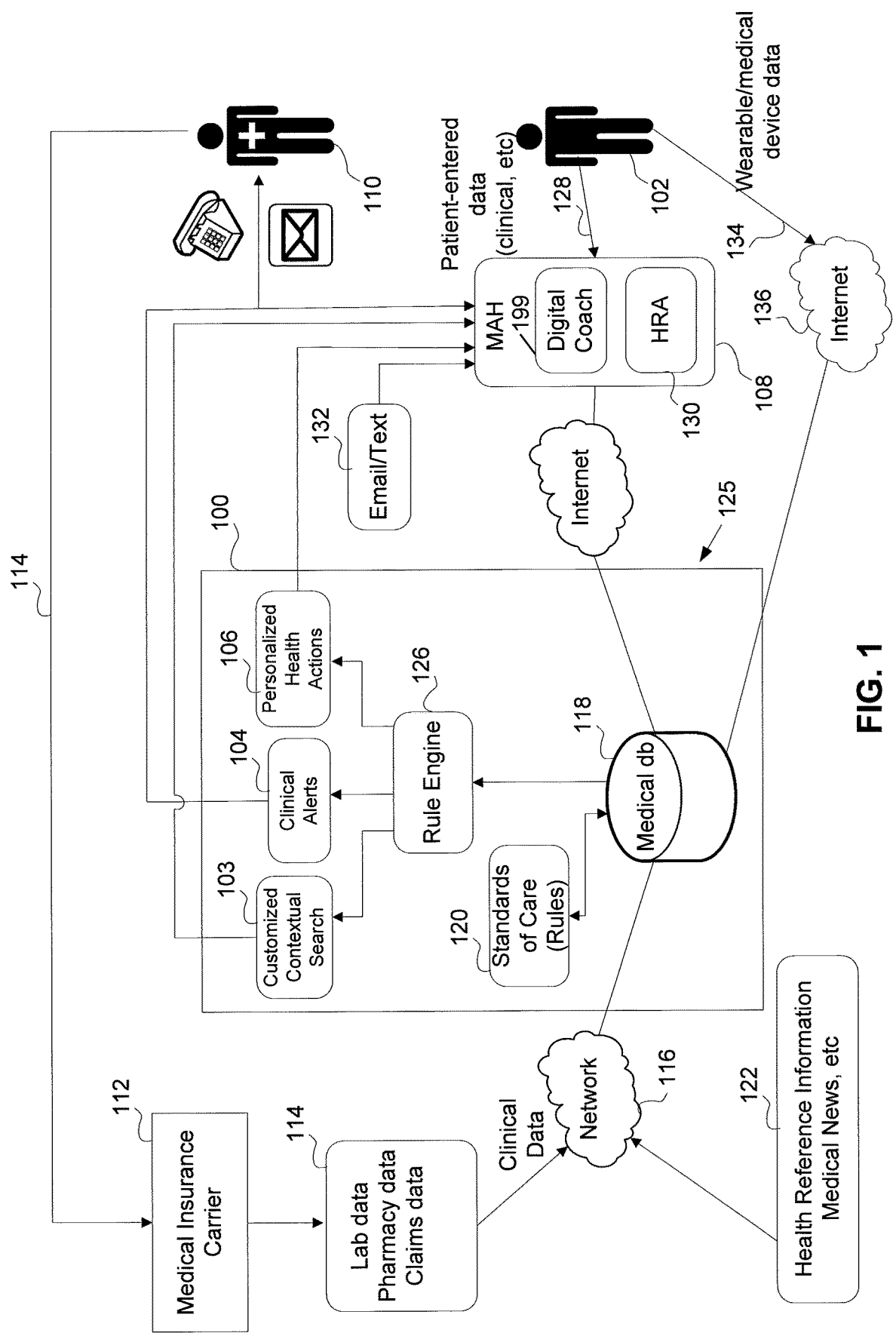
FIG. 1 is a schematic illustrating an overview of a system for generating a well-being assessment and scoring, in accordance with an embodiment of the disclosure.

The following embodiments further illustrate the disclosure but, should not be construed as in any way limiting the scope of the disclosure.

Disclosed is a system and method for generating a scoring that measures a plurality of dimensions of total well-being of a person or population, referred to herein as a "well-being scoring." The disclosed system and method can include personalized intervention strategies and reporting. The well-being scoring incorporates six (6) dimensions of well-being: (1) Physical Health, (2) Emotional Health, (3) Financial Security, (4) Social Connectedness, (5) Purpose, and (6) Character Strengths.

Physical Health includes, among other things, an indication of being sufficiently healthy to be able to carry out routine tasks in life now and into the future. Emotional Health includes, among other things, an indication of being satisfied with life, having good mental health, and being able to deal with difficult emotions. Financial Security includes, among other things, an indication of having sufficient financial resources to be able to pursue one's life goals and not overly worry about making ends meet. Social Connectedness includes, among other things, an indication of having close, meaningful, and supportive relationships and being respected by and connected to community. Purpose includes, among other things, an indication of having a sense of meaning in life, a direction to one's activities and pursuing what is most important. Character Strengths includes, among other things, an indication of having consistent thoughts and actions that contribute to the good of one self and others.

To generate the well-being scoring, the disclosed system and method receive data from various data sources, filter the data, and analyze the filtered data to compute the well-being scoring. The well-being scoring can then be used to drive personalized healthcare intervention strategies, including improving clinical outcomes and/or reducing medical spend.

In some implementations, a portion of the data used to generate the well-being scoring may be received from a medical claims database associated with a member of a healthcare organization. Another portion of the data may be self-reported by the member, such as responses to one or more questionnaires. Still further portions can come from other data sources, as described in greater detail herein.

The disclosed system and method provide for a better understanding of a member's well-being and the factors that can influence well-being. The disclosed system and method can also help to understand well-being needs of an member base or consumer population and what interventions should be put in place. The disclosed system and method can measure impact of interventions on well-being over time. The disclosed system and method can measure well-being at the individual member level and develop the ability to target interventions based on individual member needs.

Since the data being used to generate the well-being scoring comes from multiple disparate sources, it is a technical challenge to merge such disparate data. Also, because of the sheer volume of data, particularly for a member population of several million members, big data management is also an issue, e.g., computer memory, storage, and processing limitations. As disclosed in greater detail herein, embodiments of the disclosure provide technical solutions to these technical problems. For example, certain data filtering, data encryption, and data processing techniques are developed in order to merge the various disparate data sources in a manner that improves memory, storage, and/or processing requirements of the computer system to generate the well-being scoring.

Some embodiments further include presenting a patient (or "member") with an interactive self-managed care plan delivered on a computing device, such as a mobile phone, and powered by a medical rules engine, for example, the CareEngine® System operated by Active Health Management, Inc. of New York, N.Y. The disclosed system is capable of delivering personalized health actions based on expected medical standards of care to information related to the patient's actual medical care in conjunction with the generated well-being scoring. The care plan, which is managed by the patient via a mobile-optimized digital asset, enables the patient to have access to a personalized library of education on their own time and on their preferred modality. The system personalizes this digital care plan by leveraging data from claims, consumer data, health assessments, smart medical devices, lab results, and biometric screening events, for example. Embodiments of the disclosure also provide a communication component that integrates with segmentation data so that when the system transmits messages to patients, the system is messaging the patient in a tone that is consistent with the patient's consumer segment. The personalized health actions can leverage geographical information known on the patient to present the patient with a localized care plan to ensure that the information being presented is accurate and best suited to resources easily available to the patient.

In various embodiments, a health care organization collects and processes a wide spectrum of medical care information in order to establish and update the relevant medical standards of care, identify the actual medical care received by the patient, and generate and deliver customized alerts, including clinical alerts and personalized health actions, directly to the patient via an online interactive engagement platform, referred to herein as the "MyActiveHealth" (MAH) platform or "Member Engagement Platform." The medical care information collected by the health care organization comprises patient-specific clinical data (e.g., based on claims, biometric health data, wearable data, smart medical device data, health care provider, and patient-entered input), as well as health reference information, including evidence-based literature relating to a plurality of medical conditions. In addition to aggregating patient-specific medical record and clinical alert information, the MAH platform also solicits the patient's input for tracking of alert follow-up actions. Additionally, the MAH platform accepts patient input of family health history, patient's allergies, current over-the-counter medications and herbal supplements, unreported and untreated conditions, as well as input for monitoring items such as blood pressure, cholesterol, and additional pertinent medical information that is likely to be within the realm of patient's knowledge.

Any of the above-discussed data can be input into a well-being calculation engine that generates a well-being scoring for the member, as described in greater detail below. For example, a medical insurance carrier may collect clinical information originating from medical services claims, performed procedures, pharmacy data, lab results, and provides it to the health care organization. Other data can also be received by the health care organization. The data is processed by the health care organization to generate filtered data that is stored in a computer-readable medium, such as a database. The database comprises one or more data files located on a computer readable medium, such as a hard disk drive, a CD-ROM, a tape drive, or the like.

In some implementations, an on-staff team of medical professionals within the health care organization consults various sources of health reference information, including evidence-based literature, to create and continuously revise a set of clinical rules that reflect the best evidence based medical standards of care for a plurality of conditions. The clinical rules are stored in a medical database.

A person health record (PHR) within the MAH platform facilitates the patient's task of creating a complete health record by automatically populating the data fields corresponding to the information derived from the claim, pharmacy, and/or lab result-based clinical data. Preferably, the PHR gathers at least some of the patient-entered data via a health risk assessment (HRA) tool that allows user entry of family history, known chronic conditions, and other medical data, and provides an overall patient health assessment. As described in greater detail below, some embodiments include a well-being assessment, that may include assessment questions directed to a Physical Health dimension. In some embodiments, the well-being assessment may replace the HRA tool, and the HRA capabilities can be a subset of the broader well-being assessment. In some embodiments, the assessment data may include data captured by clinicians and/or coaches when working directly with patients. Preferably, the HRA tool presents a patient with questions that are relevant to his or her medical history and currently presented conditions. The risk assessment logic branches dynamically to relevant and/or critical questions, thereby saving the patient time and providing targeted results. The data entered by the patient into the HRA also populates the corresponding data fields within other areas of PHR and generates additional clinical alerts to assist the patient in maintaining optimum health. In addition, data that is captured on wearable devices, such as, for example, a Fitbit device, a Garmin device, an iHealth smart medical device (e.g., Blood Pressure Cuffs and Glucometers), among others, is also received and stored, provided that the patient has completed the authorization process to allow data to flow from the individual devices into the system.

The health care organization aggregates the medical care information, including the patient or nurse-entered data as well as claims data, biometric health information, and wearable/smart medical device data, into the medical database for subsequent processing via an analytical system, such as, for example, the CareEngine® System operated by Active Health Management, Inc. of New York, N.Y. The CareEngine® System is a multi-dimensional analytical application including a rules engine module comprising computer-readable instructions that apply a set of clinical rules reflecting the best evidence-based medical standards of care for a plurality of conditions to the patient's claims and self-entered clinical data that reflects the actual care that is being delivered to the patient. Some embodiments of the disclosure are described herein in reference to the CareEngine® System, but in other embodiments any technically feasible medical analysis engine or system may be used.

The rules engine module identifies one or more instances where the patient's actual care, as evidenced by claims data (e.g., medical procedures, tests, pharmacy data and lab results, and patient-entered clinical data) is inconsistent with the best evidence-based medical standards of care and issues patient-specific clinical alerts directly to the patient via a set of web pages comprising the PHR tool. Additionally, the rules engine module applies specific rules to determine when the patient should be notified, via the PHR, of newly available health information relating to their clinical profile. In one embodiment, the physician gains access to the web pages with the consent of the patient.

In an embodiment, when the rules engine module identifies an instance of actual care inconsistent with the established, best evidence-based medical standards of care, the patient is presented with a clinical alert via the MyActiveHealth platform. These clinical alerts are presented as a plan of care, which provides the member with a personalized digital coaching experience. In some embodiments, the clinical alerts include notifications to contact the health care provider in order to start or stop a specific medication and/or to undergo a specific examination or test procedure associated with one or more conditions and co-morbidities specific to the patient. To ensure prompt patient response, in some embodiments, the health care organization sends concurrent email notifications to the patient regarding availability of personalized health actions and/or well-being actions at the MyActiveHealth platform. The clinical alerts notify the patient regarding known drug interactions and suggested medical therapy based on the best evidence-based medical standards of care. In addition to condition specific alerts, the rules engine module notifies the patient regarding relevant preventive health information by issuing personalized health actions, via the MyActiveHealth platform. In one embodiment, the patient is able to use the MyActiveHealth platform to search for specific health reference information regarding a specified condition, test, or medical procedure by querying the medical database via a user interface. In some embodiments, the MyActiveHealth platform allows the patient to create printable reports containing the patient's health information, including health summary and health risk assessment reports, for sharing with a health care provider. This information can also be exported to an external database, such as Microsoft Healthvault.

Additionally, by functioning as a central repository of a patient's medical information, the MyActiveHealth platform empowers patients to more easily manage their own health care decisions, which is advantageous as patients increasingly move toward consumer-directed health plans.

Further embodiments include implementing a plurality of modules for providing real-time processing and delivery of clinical alerts and personalized health actions to the patient via the MyActiveHealth platform and to a health care provider via one or more health care provider applications. Specifically, the system includes a real-time application messaging module for sending and receiving real-time information via a network between the health care organization and external systems and applications. Preferably, the real-time application messaging module employs a service-oriented architecture (SOA) by defining and implementing one or more application platform-independent software services to carry real-time data between various systems and applications.

In one embodiment, the real-time application messaging module comprises web services that interface with external applications for transporting the real-time data via a Simple Object Access Protocol (SOAP) over HTTP. The message ingest web service, for example, receives real-time clinical data which is subsequently processed in real-time by the rules engine module against the best evidence-based medical standards of care. Incoming real-time data is optionally stored in the medical database.

Incoming real-time data associated with a given patient, in conjunction with previously stored data and applicable clinical rules, defines a rules engine run to be processed by the rules engine module. Hence, the real-time application messaging module collects incoming real-time clinical data from multiple sources and defines a plurality of rules engine runs associated with multiple patients for simultaneous real-time processing.

The real-time application messaging module forwards the rules engine runs to the rules engine module to instantiate a plurality of real-time rule processing sessions. The rules engine module load-balances the rule processing sessions across multiple servers to facilitate real-time matching of the clinical rules (best evidence-based medical standards of care) against multiple, simultaneous requests of incoming clinical data and patient-entered data. When the actual mode of care for a given patient deviates from the expected mode of care, the rules engine module generates one or more clinical alerts. Similarly, the rules engine module generates real-time personalized health actions based on the best evidence-based medical standards of preventive health care.

During processing, the rules engine module records alert justification information in the medical database. In one embodiment, the alert justification information specifies which clinical rules have been triggered/processed by the incoming data (e.g., by rule number), which alerts have been generated (e.g., by alert number), a time/date stamp for each alert, the specific exclusionary and inclusionary information for a given patient that caused the rule to trigger (e.g., known drug allergies are used to exclude alerts recommending a drug regimen that may cause an allergic reaction), as well as patient-entered and claim information associated with the incoming real-time data that triggered a given rule.

In yet another embodiment, the rules engine module analyzes patient specific clinical data to generate a real-time risk score for various medical conditions. The risk score quantifies the severity of existing medical conditions and assesses the risk for future conditions in light of evaluating multiple risk factors in accordance with the clinical rules. For example, the risk score may identify high risk diabetics or patients subject to a risk of future stroke. The system presents the risk score to the patient, as well as to the health care provider.

Therefore, each rule processing session produces a plurality of clinical alerts, personalized health actions, and/or calculates a risk score based on a set of real-time data for a given patient. The message transmit web service, in turn, delivers the generated alerts to the PHR and/or health care provider applications. Alternatively, the application messaging module comprises a single web service for both sending and receiving real-time data. To facilitate the real-time delivery of alerts, the alert payload filtering module reduces the real-time alert payload by filtering the alert input to the real-time application messaging module by a plurality of conditions and categories. In addition to improving the speed of real-time delivery of alerts, alert filtering eliminates redundant alerts and helps to focus the recipient's attention on the important alerts.

In another embodiment, patient care management functionality is implemented. The disclosure includes querying a set of clinical rules and obtaining claims data containing clinical information relating to a plurality of patients. The system can identify patients that would benefit from care management and create a listing of markers, or conditions, associated with each identified patient based on the claims data containing clinical information relating to the patient. The system generates an individual care plan for a patient base on the identified markers, goals, problems, vision goals and the claims data containing clinical information relating to the patient, which may include diagnosis information that may accompany the claims data.

In another embodiment, information about occurrences of when the rules engine module identifies an instance of actual care inconsistent with the established, best evidence-based medical standards of care is transmitted to a well-being scoring calculation engine that uses this data, among others, to compute a well-being scoring for the member.

Turning to FIG. 1, an implementation of a system contemplated by an embodiment of the disclosure is shown with reference to an automated system for generating a scoring that measures a plurality of dimensions of total well-being of person or population. In some embodiments, the system is also capable of presenting a patient with an interactive digital coaching experience powered by clinical decision support technology capable of delivering personalized health actions (including clinical alerts called "Care Considerations") based on comparison of the best evidence-based medical standards of care to a patient's actual medical care. A health care organization 100 collects and processes a wide spectrum of medical care information relating to a patient 102 in order to generate and deliver customized alerts, including clinical alerts 104 and personalized health actions 106 both of which are used to drive a personalized digital coaching experience, directly to the patient 102 via an online interactive engagement platform 108, referred to herein as MyActiveHealth (MAH) 108. In addition to aggregating patient-specific medical records and alert information, as well as other functionality to be discussed herein, MAH 108 also solicits input from the patient 102 for entering additional pertinent medical information, tracks alert follow-up actions, and allows the health care organization 100 to track alert outcomes.

When the patient 102 utilizes the services of one or more health care providers 110, a medical insurance carrier 112 collects the associated clinical data 114 in order to administer the health insurance coverage for the patient 102. Additionally, a health care provider 110, such as a physician or nurse, enters clinical data 114 into one or more health care provider applications pursuant to a patient-health care provider interaction during an office visit or a disease management interaction. Clinical data 114 originates from medical services claims, pharmacy data, as well as from lab results, and includes information associated with the patient-health care provider interaction, including information related to the patient's diagnosis and treatment, medical procedures, drug prescription information, in-patient information and health care provider notes. The medical insurance carrier 112 and the health care provider 110, in turn, provide the clinical data 114 to the health care organization 100, via one or more networks 116, for storage in a medical database 118. The medical database 118 is administered by one or more server-based computers associated with the health care provider 100 and comprises one or more medical data files located on a computer-readable medium, such as a hard disk drive, a CD-ROM, a tape drive or the like. The medical database 118 preferably includes a commercially available database software application capable of interfacing with other applications, running on the same or different server based computer, via a structured query language (SQL). In an embodiment, the network 116 is a dedicated medical records network. Alternatively or in addition, the network 116 includes an Internet connection which comprises all or part of the network.

An on-staff team of medical professionals within the health care organization 100 consults various sources of health reference information 122, including evidence-based preventive health data, to establish and continuously or periodically revise a set of clinical rules 120 that reflect best evidence-based medical standards of care for a plurality of conditions. The clinical rules 120 are stored in the medical database 118. This process ensures that new or modified evidence based medical standards can be incorporated into the digital coaching experience 199.

To supplement the clinical data 114 received from the insurance carrier 112, MAH 108 allows patient entry of additional pertinent medical information that is likely to be within the realm of patient's knowledge. Exemplary patient-entered data 128 includes additional clinical data, such as patient's family history, use of non-prescription drugs, known allergies, unreported and/or untreated conditions (e.g., chronic low back pain, migraines, etc.), as well as results of self-administered medical tests (e.g., periodic blood pressure and/or blood sugar readings). In some embodiments, MAH 108 facilitates the patient's task of creating a complete health record by automatically populating the data fields corresponding to the information derived from the medical claims, pharmacy data, and lab result-based clinical data 114. In one embodiment, patient-entered data 128 also includes non-clinical data, such as upcoming doctor's appointments. In some embodiments, the patient-entered data 128 also includes responses to one or more questionnaires.

In some embodiments, MAH 108 gathers at least some of the patient-entered data 128 via a health risk assessment tool (HRA) 130 that requests information regarding lifestyle behaviors, family history, known chronic conditions (e.g., chronic back pain, migraines) and other medical data, to flag individuals at risk for one or more predetermined medical conditions (e.g., cancer, heart disease, diabetes, risk of stroke) pursuant to the processing by the rules engine module 126. The HRA 130 data gathering process can be expanded to incorporate a broader scope of questions as we implement the well-being assessment. The incremental data may also be connected to CareEngine® System 125 to generate recommended health actions related to well-being. In some embodiments, the HRA 130 presents the patient 102 with questions that are relevant to his or her medical history and currently presented conditions. The risk assessment logic branches dynamically to relevant and/or critical questions, thereby saving the patient time and providing targeted results. The data entered by the patient 102 into the HRA 130 also populates the corresponding data fields within other areas of MAH 108. The health care organization 100 aggregates the clinical data 114, patient-entered data 128, as well as the health reference and medical news information 122, into the medical database 118 for subsequent processing via the rules engine module 126.

The analytical system, for example, the CareEngine® System 125, is a multi-dimensional analytical software application including a rules engine module 126 comprising computer-readable instructions for applying a set of clinical rules 120 to the contents of the medical database 118 in order to identify an instance where the patient's 102 actual care, as evidenced by the clinical data 114 and the patient-entered data 128, is inconsistent with the best evidence-based medical standards of care. After collecting the relevant data 114 and 128 associated with the patient 102, the rules engine module 126 applies the clinical rules 120 specific to the patient's medical data file, including checking for known drug interactions, to compare the patient's actual care with the best evidence-based medical standard of care. In addition to analyzing the claims and lab result-derived clinical data 114, the analysis includes taking into account known allergies, chronic conditions, untreated conditions and other patient-reported clinical data to process and issue condition-specific clinical alerts 104 and personalized health actions 106 directly to the patient 102 via a set of web pages in MAH 108. The rules engine module 126 is executed by a computer in communication with the medical database 118. In one embodiment, the computer readable instructions comprising the rules engine module 126 and the medical database 118 reside on a computer readable medium of a single computer controlled by the health care organization 100. Alternatively, the rules engine module 126 and the medical database 118 are interfacing via separate computers controlled by the health care organization 100, either directly or through a network.

To ensure prompt patient response, the health care organization 100 preferably sends concurrent email notifications 132 to the patient 102 regarding availability of customized digital alerts 104 (e.g., digital coaching alerts and/or heath event alerts) and personalized health actions 106 at MAH 108. As described herein, the terms "alerts" and "customized alerts" refer to patient-specific health related notifications, such as clinical alerts 104 and personalized health actions 106, which have been delivered directly to the patient 102 via MAH 108 after being generated by the rules engine module 126 pursuant to the processing of one or more of the clinical data 114 and patient-entered data 128, and matched with the best evidence-based medical standards of care reflected in the clinical rules 120. In an embodiment, the alerts 104, 106 are also delivered to the health care provider 110. When the rules engine module 126 identifies an instance of actual care which is inconsistent with the best evidence-based medical standards of care, the patient 102 is presented with a clinical alert 104 via MAH 108.

In some embodiments, the clinical alert may be associated with a "health event." A health event, as used herein, represents a specific event in a patient's health journey. Examples of health events could include: a new diagnosis of a chronic condition, an abnormal lab result, or starting a new prescription drug, among others. The rule engine 126 is configured to detect such health events based on the patient's medical data stored in medical database 118, and the MAH 108 is configured to provide the patient 102 with an experience that walks the patient 102 through their specific health event.

In some embodiments, the clinical alerts 104 are prominently displayed as personalized health actions within a user interface of MAH 108. In embodiments, the clinical alerts 104 include notifications to contact the health care provider 110 in order to start or stop a specific medication and/or to undergo a specific test procedure associated with one or more conditions and co-morbidities specific to the patient 102. The clinical alerts 104 include notifying the patient regarding known drug interactions and suggested medical therapy derived from the current best evidence-based medical standard of care information 120. The clinical alerts 104 are also prompted by analysis of patient's medication regimen in light of new conditions and lab results. The alerts 104 are used as a method to provide a curated, personalized digital coaching experience 199 to patients that they can manage at their own pace through a variety of different types of content that the patient can complete Similarly, the rules engine module 126 notifies the patient 102 regarding the clinically relevant preventive health information 122 by issuing personalized health actions 106, via MAH 108, to ensure overall consistency of care.

The rules engine module 126 also identifies the members who have at risk lifestyle behaviors (e.g., smoking, high stress, poor diet/exercise) and seeks consent from the high risk members to enroll them in a lifestyle coaching program. In one embodiment, the patient 102 is able to use the curated digital coaching experience 199 to educate themselves on different aspects of the identified lifestyle behaviors. The content assigned to the member is personalized and relevant based upon the data known for the member and stored in the database.

In yet another embodiment, the rules engine module 126 automatically generates a customized contextual search 103 of the health reference information 122, and/or an external source of medical information, based on the patient's clinical data 114 and patient-entered data 128 for delivery of the search results via MAH 108. In yet another embodiment, the patient 102 receives general health reminders based on non-clinical components of the patient-entered data 128 that are not processed by the rules engine module 126, such as notifications regarding upcoming doctor appointments. In embodiments, the general health reminders include prompting the patient 102 to update the HRA 130, watch a video tour of the MyActiveHealth platform, or update the health tracking information (discussed below in connection with FIG. 16). Preferably, the PHR allows the patient 102 to create printable reports containing the patient's health information, including health summaries and health risk assessment reports, for sharing with the health care provider 110.

Still further, in some embodiments, device data 134 is captured on wearable devices, such as, for example, a smart watch, a fitness tracker (e.g., a Fitbit device), an activity tracker (e.g., a Garmin device), a medical device (e.g., an iHealth smart medical device, blood pressure cuffs, or glucometers, etc.), among others, and is transmitted over a network 136 to be stored in the database 118. In some embodiments, before the device data 134 is transferred to the database 118, the patient completes an authorization process to allow sharing of the device data 134.

To ensure further follow-up, the health care organization 100 optionally notifies the health care provider 110 regarding the outstanding clinical alerts 104. For example, if a clinical alert 104 includes a severe drug interaction, the health care organization 100 prompts the health care provider 110, via phone, mail, email, live chat, nurse messaging, nurse appointment scheduling, or other communications, to initiate immediate follow-up.

While the entity relationships described above are representative, those skilled in the art will realize that alternate arrangements are possible. In one embodiment, for example, the health care organization 100 and the medical insurance carrier 112 is the same entity. Alternatively, the health care organization 100 is an independent service provider engaged in collecting, aggregating and processing medical care data from a plurality of sources to provide a personal health record (PHR) service for one or more medical insurance carriers 112. In yet another embodiment, the health care organization 100 provides PHR services to one or more employers by collecting data from one or more medical insurance carriers 112.

Figure 2:
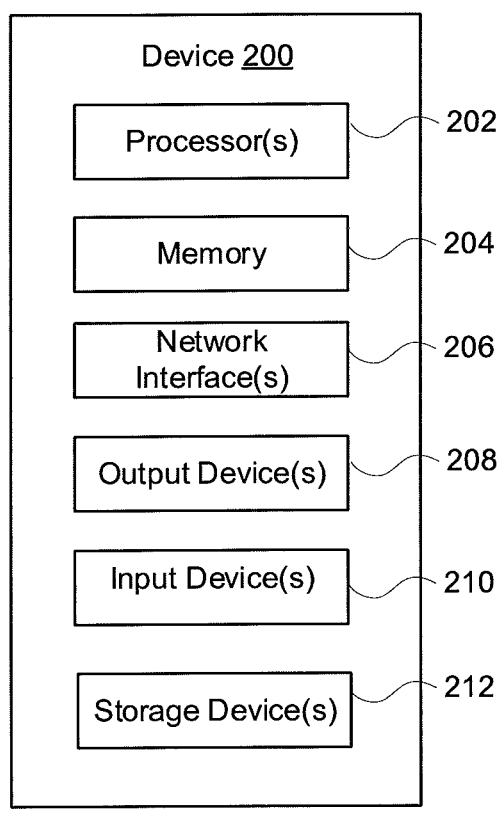
FIG. 2 illustrates a computing device, according to an embodiment of the disclosure.

FIG. 2 is a block diagram illustrating basic hardware components of a computing device that may be used as servers, databases, member devices, health care organization 100 computing devices, according to some example embodiments. Device 200 may include one or more processors 202, memory 204, network interfaces 206, output devices 208, input devices 210, and storage devices 212. Although not explicitly shown in FIG. 2, each component provided is interconnected physically, communicatively, and/or operatively for inter-component communications in order to realize functionality ascribed to the member devices, health care organization 100 devices, and servers in the system of FIG. 1. To simplify the discussion, the singular form will be used for all components identified in FIG. 2 when appropriate, but the use of the singular does not limit the discussion to only one of each component. For example, multiple processors may implement functionality attributed to processor 202.

Processor 202 is configured to implement functions and/or process instructions for execution within the device 200. For example, processor 202 executes instructions stored in memory 204 or instructions stored on a storage device 212. In certain embodiments, instructions stored on storage device 212 are transferred to memory 204 for execution at processor 202. Memory 204, which may be a non-transient, computer-readable storage medium, is configured to store information within the device 200 during operation. In some embodiments, memory 204 includes a temporary memory that does not retain information stored when the device 200 is turned off. Examples of such temporary memory include volatile memories such as random access memories (RAM), dynamic random access memories (DRAM), and static random access memories (SRAM). Memory 204 also maintains program instructions for execution by the processor 202 and serves as a conduit for other storage devices (internal or external) coupled to the device 200 to gain access to processor 202.

Storage device 212 includes one or more non-transient computer-readable storage media. Storage device 212 is provided to store larger amounts of information than memory 204, and in some instances, configured for long-term storage of information. In some embodiments, the storage device 212 includes non-volatile storage elements. Non-limiting examples of non-volatile storage elements include floppy discs, flash memories, magnetic hard discs, optical discs, solid state drives, or forms of electrically programmable memories (EPROM) or electrically erasable and programmable (EEPROM) memories.

Network interfaces 206 are used to communicate with external devices, computers, and/or servers. The device 200 may include multiple network interfaces 206 to facilitate communication via multiple types of networks. For example, health care organization 100 can include multiple servers connected through their network interfaces to facilitate sharing of information and making requests among the multiple servers. Network interfaces 206 may include network interface cards, such as Ethernet cards, optical transceivers, radio frequency transceivers, or any other type of device that can send and receive information. Non-limiting examples of network interfaces 206 include radios compatible with several Wi-Fi standards, 3G, 4G, Long-Term Evolution (LTE), Bluetooth®, etc.

The device 200 may also be equipped with one or more output devices 208. Output device 208 is configured to provide output to a user using tactile, audio, and/or video information. Examples of output device 208 may include a display (e.g., liquid crystal display (LCD) display, light emitting diode (LED) display, organic LED (OLED) display, microLED (mLED) display, quantum dot display, etc.), a sound card, a video graphics adapter card, speakers, magnetics, or any other type of device that may generate an output intelligible to a user of the device 200.

The device 200 may also be equipped with one or more input devices 210. Input devices 210 are configured to receive input from a user or the environment where the device 200 resides. In certain instances, input devices 210 include devices that provide interaction with the environment through tactile, audio, and/or video feedback. These may include a presence-sensitive screen or a touch-sensitive screen, a mouse, a keyboard, a camera, a microphone, a voice responsive system, or any other type of input device.

The hardware components described thus far for the device 200 are functionally and communicatively coupled to achieve certain behaviors. In some embodiments, these behaviors are controlled by software running on an operating system of the device 200.

As described above, disclosed is a system and method for generating a well-being scoring that measures a plurality of dimensions of total well-being of a person or population. The disclosed system and method can include personalized intervention strategies and reporting. The well-being scoring incorporates six (6) dimensions of well-being: (1) Physical Health, (2) Emotional Health, (3) Financial Security, (4) Social Connectedness, (5) Purpose, and (6) Character Strengths.

In one embodiment, each of the six dimensions (i.e., Physical Health, Emotional Health, Financial Security, Social Connectedness, Purpose, and Character Strengths) is evaluated separately to generate a score for that dimension. Then, the scores from the six dimensions are aggregated to generate the well-being scoring. In another embodiment, less than all six dimensions are used to generate the well-being scoring. In a still further embodiment, an additional dimension on top of the six referenced above may also be used.

Figure 3:
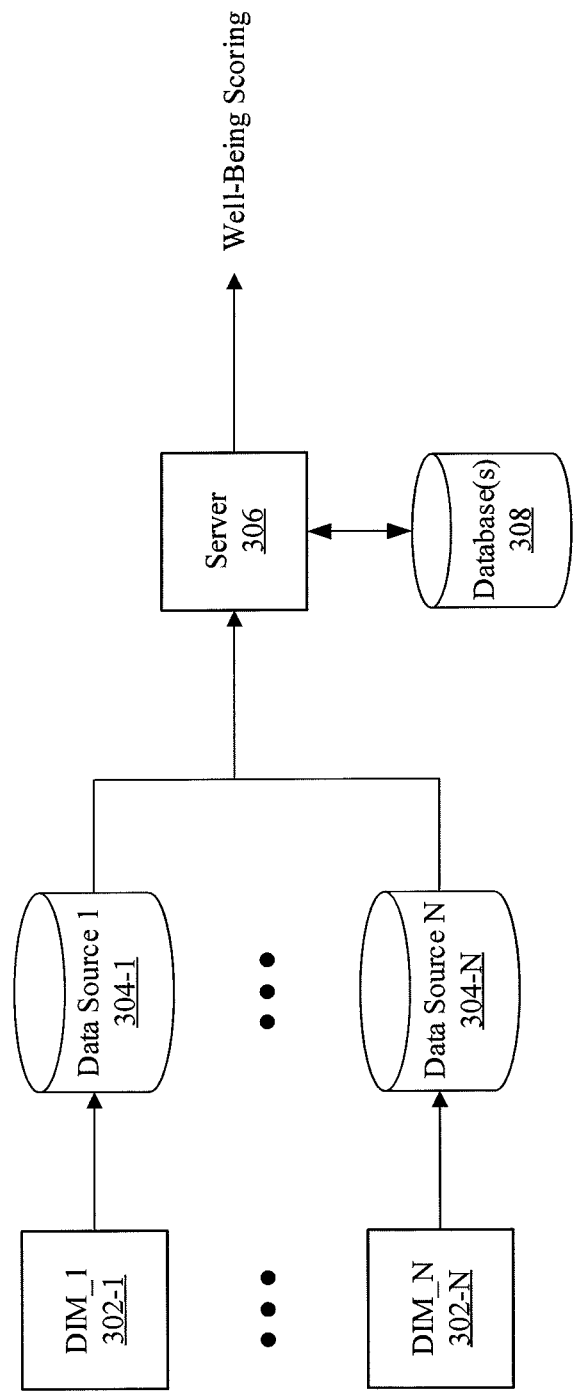
FIG. 3 is a block diagram illustrating generating the well-being scoring, according to one embodiment.

FIG. 3 is a block diagram illustrating generating the well-being scoring, according to one embodiment. For each of N dimensions 302-1 to 302-N that are evaluated, data is received from a data source 304-1 to 304-N, respectively. Each data source 304-1 to 304-N may comprises one or more servers or databases. In some embodiments, multiple data sources may comprises data used to compute one of the dimensions. In further embodiments, the same data source may comprises data used to compute two or more of the dimensions.

The data for the N dimensions is transmitted to a server 306 and stored in a database 308. The server 306 may comprise one or more processors configured to analyze the data to generate the well-being scoring. Additional detail related to how the data is stored and processed is described below. For example, the data may be processed and filtered before being stored in the database, in order to minimize memory, storage, and processing resources used to compute the well-being scoring.

An objective of the well-being scoring is to help members and consumers better understand the factors that can impact their well-being across each dimension and guide recommended interventions. For example, assessment questions can be provided to a member to answer that cover the six dimensions of well-being. The questions may also be included to identify member engagement or focus area preferences for enhanced personalization of recommended interventions. Doing so supports the evaluation of well-being needs at the individual and enterprise level, and progress tracking over time.

The well-being assessment and scoring can allow the disclosed system to identify gaps and barriers impacting the well-being of members. The disclosed system provides interventions to help improve well-being. Members or consumers may choose not to act upon our recommendations, and exogenous factors may adversely impact individual and/or population level results. The data gathered through the assessment can establish a baseline that can be monitored over time. Those measurements may include a focus on changes in physical health, which can be further validated and measured using claim data and other health metrics.

Once the well-being scoring is generated, the well-being scoring can be used to provide personalized well-being paths. The server 306 may be able to offer targeted and personalized plans to enhance the total well-being of individuals and populations. The server 306 can provide automated and personalized alignment of relevant well-being support resources or programs with members based on their well-being scoring, questionnaire responses, scores or other relevant data. Prioritization and sequencing of recommendations can rely on well-being scoring and other data (self-reported or other) or algorithms designed to personalize the experience and optimize member engagement. Prioritization or sequencing can also be used to coordinate interventions being offered across multiple dimensions and programs.

Some embodiments for personalizing well-being activities may include evaluating factors related to severity of need, sequencing of recommendations to support ongoing engagement and growth, analyzing relative importance or preference by dimension, and/or segmentation based on engagement channel preferences or other factors based on available data. The server 306 may also evaluate data such as age, family status, financial status, and other factors to align the appropriate resource with each individual through markers or development of algorithms.

An intervention strategy can be established aligning relevant resources with members based on their well-being scoring, considering appropriate relative importance and order based on member scoring. In some embodiments, well-being recommendations may also be triggered based on specific assessment responses or may be broadly made available to members. Interventions include existing physical health, wellness, and behavioral health content. A library of interventions can be used to support the new well-being dimensions. Interventions may include recommended actions, questionnaires, programs, tools, and external support resources for example. Prioritization and sequencing of recommendations can rely on scoring and potentially other data or algorithms to personalize the experience and optimize member engagement. Interventions may apply across multiple dimensions. Members can determine which recommended interventions will help them improve their well-being in the specific dimensions they choose to focus on.

Individual well-being reports and display members may include a personalized dashboard that features action steps and interventions for each dimension prioritized by greatest risk areas. Some embodiments provide the ability for plan sponsors to integrate their companies' programs and interventions specific to each dimension.

Individual well-being results for members and consumers can be presented through both mobile and web experiences. This includes a personalized dashboard that features scoring results for overall well-being and scores by dimension, as well as recommended action steps and additional intervention resources for each dimension. Recommended actions can be prioritized by greatest risk (lowest score) areas. Members can also view available intervention resources by dimension and self-direct their path to well-being. Plan sponsors may have the ability to integrate additional intervention resources, such as company programs specific to each dimension Well-Being Assessment As described above, in one embodiment, the data corresponding to a particular dimension of well-being may be based on responses to a questionnaire or assessment. The assessment may include well-being question and answer pairs reflecting the six dimensions, as well as additional research questions, and survey feedback questions. In some embodiments, the scores may be calculated without using any research questions. In one embodiment, instead of asking assessment questions for the Physical Health dimension, a score for the Physical Health dimension can be based on medical data and/or self-reported data for the member in a medical database, such as using a health index, such as for example the Aetna ActiveHealth Index, as described in greater detail below.

For each dimension of the well-being scoring, a model is developed for scoring the dimension. Then another model is used to aggregate the scores from the different dimensions to achieve the well-being scoring.

"Character Strengths" as a Dimension of Well-Being

In some embodiments, Character Strengths are characteristics for effective individual and community functioning aligning thought and action with a coherent life in order to promote good. The core of character strengths has traditionally been understood as practical wisdom, justice, courage, and capacity for moderation. All other character strengths are thought in some way to depend on these four.

Character strengths are strongly predictive of subsequent life outcomes. For example, the capacity for delayed gratification is important for many aspects of health and well-being. For example, four-year old children can be offered a marshmallow but told that if they waited for fifteen minutes they could have two. The number of minutes the four-year old child was able to wait may be strongly predictive of subsequent SAT test scores, social functioning, and emotional regulation more than ten years later. "Seeking to do good" was one of the strongest well-being predictors of job engagement, quality of work, and job satisfaction.

A whole industry has grown up around character development. Many schools now include curriculum for character skills, sometimes in the form of life skills training. Career development and leadership training often now also include teaching character strengths. Some health care organizations have invested in mindfulness which is an important pathway to the development of character strengths.

Character has been viewed as a part of well-being in the vast majority of the Western philosophical tradition, and arguably also worldwide. Including a character dimension in the well-being scoring circumvents this critique and addresses what has been acknowledged for centuries as something that plays a role in well-being.

Character strengths contribute to the well-being of not only oneself, but also of others. The disclosed dimensions of well-being can be focused principally on the individual. The character strengths dimension certainly contributes to, and is a part of, individual well-being but it also contributes to the well-being of others.

Including a character strengths dimension distinguishes the disclosed well-being scoring from many other indicators of health. While character strengths have now become increasingly studied and recognized as an important dimension of well-being, existing indices still generally exclude it. The study of character strengths has become an increasingly prominent area of research in positive psychology, and the disclosed well-being scoring is leading and incorporating this work far beyond the existing indices.

In summary, the character strength dimension (i) increases the predictive capacity of the scoring for numerous life outcomes, (ii) effectively measures what many training and development programs intend to promote, (iii) includes what is clearly an important dimension of human life and would address some of the increasingly strong critiques of the social science of well-being, (iv) promotes further well-being of the entire community in addition to individuals and (v) makes Aetna a true leader in the well-being field.

Some example assessment questions to assess character strengths may include:

Q1. I always act to promote good in all circumstances, even in difficult and challenging situations. (0=Not True of Me; 10=Completely True of Me)

Q2. After some reflection, I always know how to bring about the most important good. 0=Not True of Me; 10=Completely True of Me)

Q3. I always treat everyone in a way that is right and good. (0=Not True of Me; 10=Completely True of Me)

Q4. I am always able to give up some happiness now for greater happiness later (0=Not True of Me; 10=Completely True of Me)

Q5. I do not try to escape difficulties when it is possible to do some good (0=Not True of Me; 10=Completely True of Me)

Q6. I give up personal pleasures whenever it is possible to do some good instead (0=Not True of Me; 10=Completely True of Me)

Q7. I get to use my character strengths to help others (0=Not True of Me; 10=Completely True of Me)

Q8. I get to do what I am good at every day (0=Not True of Me; 10=Completely True of Me)

Scoring Approaches

Various approaches to scoring within across multiple dimensions of well-being to generate the well-being scoring and/or scoring within one dimension are within the scope of the disclosure.

A first embodiment provides equal scoring within dimensions and equal weighting across dimensions. This approach has the advantage of simplicity. For example, one dimension may have a given number of data items associated with that dimension, each of which has a range of scores. For example, the range of scores can be 1 to 10 per data item. In some embodiments, different data items have different ranges of scores. In such a case, the ranges of the various data items can be scaled to match the ranges of the other data items in the dimension, e.g., 1 to 10. In one implementation, the well-being scoring may be rounded to the closest integer, or may have one decimal point, e.g., 7.6 or 8.2, etc.

In embodiments where the Physical Health dimension is based on medical data, the score that is based on the medical data can be scaled to the same range as the other dimensions. For example, the Aetna "ActiveHealth Index" (AHI), described in greater detail below, may be used for the Physical Health dimension score. The ActiveHealth Index may have a maximum and minimum value, for example, 100 and 0, respectively. If the other dimensions have a range of 1 to 10, the Physical Health dimension score can be scaled based on the member's actual ActiveHealth Index score and minimum and maximum possible ActiveHealth Index scores using the following equation:

$$\text{Physical Health score} = 10 \left( \frac{\text{Actual ActiveHealth Score} - \text{Minimum ActiveHealth Score}}{\text{Maximum ActiveHealth Score} - \text{Minimum ActiveHealth Score}} \right)$$

Depending on how the ActiveHealth Index is calculated, further calibration of the scaling for the ActiveHealth Index may be desirable.

To compute a score for a dimension, assuming that the ranges of each data item in the dimension have been normalized to the same range, an average score across the data items can be computed. Then, to compute the well-being scoring across multiple dimensions, the scores for each dimension can be averaged to generate the well-being scoring.

Example data items can be responses to assessment questions that provide answer choices in a particular range, e.g., 1 to 10. Other example data items may be based on data from a medical claims database or other data source.

A second embodiment for scoring provides equal scoring within dimensions, but different weighting across dimensions. In one implementation, each member can set the weights for each dimension based on the member's subjective assessment of the importance of each dimension. In another implementation, a health care organization (e.g., insurance company) can set the weights for each dimension. The second embodiment has the advantage of taking into account what a member (or health care organization) considers important.

A third embodiment for scoring provides weighting of data items within a dimension and weighting across dimensions. For example, where the data items within a dimension include responses to questions, certain questions may be weighted more heavily than others. In various embodiments, the weights may be determined by members themselves or by a health care organization.

A fourth embodiment for scoring provides use of factor analysis and modeling to suggest scoring within dimensions and weighting across dimensions. This approach has the advantage of using data and empirical correlations across data items within a dimension and across dimensions to determine whether certain data items or certain dimensions correlate particularly strongly with the others and are thus more strongly related to a well-being construct. Any computerized predictive data analytics technique can be used to perform the factor analysis, such as a deep neural network.

Regardless of which scoring scheme is used, the scoring can be further refined through incorporation of additional data types associated with these new dimensions of well-being over time. Also, the scoring mechanism could be updatable in real-time to support display of well-being assessment results to members and consumers through digital tools following completion of or update of a well-being assessment.

ActiveHealth Index

The ActiveHealth Index (AHI) is a numerical metric that reflects the health of a member or population and is associated with health care cost and utilization. The AHI can be used as the value for the Physical Health dimension when computing the overall well-being scoring.

The AHI is measured as a weighted aggregate of several components including, for example:
A. age and gender
B. a member's own perception of Health,
C. presence of Minor Conditions (e.g., from "CareEngine" (CE) markers),
D. presence of Major Conditions (e.g., from CE Markers),
E. comorbidities (e.g., from CE Markers),
F. at risk conditions (e.g., from CE Markers),
G. presence of Lifestyle Risks (e.g., from HRA, care management data, CE markers),
H. biometrics (e.g., from CE),
I. socioeconomic (e.g., from Eligibility, ODS),
J. preventive care,
K. health opportunities (e.g., from CE markers, open Care Considerations),
L. medication adherence (e.g., from CE markers), and/or
M. behavioral health conditions (e.g., from CE markers).

When computing the ActiveHealth Index, the highest score (for example, 100) represents the optimal state of health and the lowest score (for example, 0) represents the worst possible state of health.

In some embodiments, two levels of regression analysis may be used to develop the infrastructure of the model. A first level develops the point scales within each component (for component with multiple data items). The second level develops the factor weighting values that determine the relative contribution of each component's contribution to the ActiveHealth Index score.

In various embodiments, the weighting within a component and the weighting of component scores to their contribution to the overall ActiveHealth Index are tied to their contribution to total medical cost. In some embodiments, the ActiveHealth Index has an inverse relationship with medical cost, i.e., the higher ActiveHealth Index, the lower the expected medical spend.

The ActiveHealth Index includes two types of components: "impactable" components and "non-impactable" components. Impactable components are components that can be improved (e.g., quitting smoking), whereas non-impactable components cannot be changed (e.g., a person's age). The disclosed system and method can provide value to members by offering programs and services that influence the impactable components of the ActiveHealth Index. The impact leads to improved health and reduced risks with the consequent reduction in utilization and health care costs.

Impactable components can be improved by population health management programs and initiatives. Non-impactable components are included in computing the ActiveHealth Index, since they provide an understanding of what is driving the health status of the population, but they are static values at any moment in time. The potential for improvement can be established by examining the scores on the impactable components to determine how much room for improvement there is if these scores were optimized. This is reflected in the calculation of an "Ideal Health Scoring," which is the score that could be achieved if the scores on all the impactable components were optimized. This enables the client to set-up realistic expectations of potential improvement based on the unique characteristics of their population.

Each of the components A-M identified above can be assigned an AHI (ActiveHealth Index) score that can have a certain range, e.g., 0 to 100. The scores from the various components are then aggregated, as described in greater detail below. Scoring of each individual component A-M is also discussed in greater detail. The point tables shown for the components A-M are merely examples, and any point structure is within the scope of the disclosure.

A. Age/Gender

The score for a member's age and gender can be determined from the age/gender scoring in accordance with the example in Table 1. AHI points, for example on a scale of 0 to 100, can be assigned for age/gender scoring in accordance with Table 2. The values in Tables 1 and 2 are merely examples and any numbers are within the scope of the disclosure.

TABLE 1

| | Gender | |
|---|---|---|
| Age Band | Female Medical Age/Gender Scoring | Male Medical Age/Gender Scoring |
| <1 | 2.8463 | 3.2383 |
| 1-4 | 0.3949 | 0.4717 |
| 5-9 | 0.2127 | 0.2576 |
| 10-14 | 0.2344 | 0.2369 |
| 15-19 | 0.3746 | 0.3280 |
| 20-24 | 0.5374 | 0.2839 |
| 25-29 | 0.7988 | 0.3183 |
| 30-34 | 0.9270 | 0.3986 |
| 35-39 | 0.9135 | 0.4995 |
| 40-44 | 0.9635 | 0.6373 |
| 45-49 | 1.0730 | 0.8042 |
| 50-54 | 1.2861 | 1.1355 |
| 55-59 | 1.4310 | 1.4794 |
| 60-64 | 1.7004 | 1.9890 |
| 65-69 | 1.6177 | 1.9944 |
| 70-74 | 1.1323 | 1.8573 |
| 75+ | 0.4732 | 1.0178 |

TABLE 2

| A/G Scoring | AHI Points |
|---|---|
| <0.3 | 100 |
| 0.6 | 90 |
| 0.9 | 80 |
| 1.2 | 70 |
| 1.5 | 60 |
| 1.8 | 50 |
| 2.1 | 40 |
| 2.4 | 30 |
| 2.7 | 20 |

TABLE 2-continued

| A/G Scoring | AHI Points |
|---|---|
| 3 | 10 |
| >3.0 | 0 |

B. Perception of Health

A member's perception of their own health can be asked in an assessment question, such as "In general, would you say your health is?" The system assigns AHI points as indicated in Table 3 for the possible responses:

TABLE 3

| HRA Response | AHI Points |
|---|---|
| Excellent | 100 |
| Very good | 75 |
| Good | 50 |
| Fair | 25 |
| Poor | 0 |

C. Minor Chronic Conditions

In one embodiment, CareEngine® markers grade a member's medical conditions as to whether the condition is considered to be major or minor. Table 4 is an example of assignment AHI points to counts of minor conditions

TABLE 4

| Number of Minor Conditions | AHI Points |
|---|---|
| 0 | 100 |
| 1 | 80 |
| 2 | 60 |
| 3 | 40 |
| 4 | 20 |
| 5 or more | 0 |

D. Major Chronic Conditions

Table 5 is an example of assignment AHI points to counts of major conditions.

TABLE 5

| Number of Major Conditions | AHI Points |
|---|---|
| 0 | 100 |
| 1 | 60 |
| 2 | 30 |
| 3 | 15 |
| 4 or more | 0 |

E. Comorbidities

In some embodiments, CareEngine® markers can be tagged as comorbidities if they contribute to a member's health status or not. The comorbidities can be refreshed at given time intervals, e.g., monthly. An example point assignment for the presence of comorbidities is found in Table 6.

TABLE 6

| Number of Comorbidities | AHI Points |
|---|---|
| 0 | 100 |
| 1 or 2 | 75 |

TABLE 6-continued

| Number of Comorbidities | AHI Points |
|---|---|
| 3 or 4 | 50 |
| 5 or 6 | 25 |
| more than 6 | 0 |

F. At-Risk Conditions

In some embodiments, CareEngine® has a set of rules that determine when a member is "at-risk" for a condition, procedure, or utilization. An example point assignment for the presence of at-risk flags is found in Table 7.

TABLE 7

| Number of At-Risk Flags | AHI Points |
|---|---|
| 0 | 100 |
| 1 | 75 |
| 2 | 50 |
| 3 | 25 |
| more than 3 | 0 |

G. Lifestyle Risks

In some embodiments, lifestyle risks comprise certain risk factors that may contribute to negative health. Some examples are found in Table 8 below. Risk factors are shown in the left column, and high risk conditions corresponding to the risk factors are shown in the right column. If a member satisfies the high risk condition for a risk factor, that adds to the count of the number of risks. AHI points can be assigned based on the total count of risk in the example in Table 9.

TABLE 8

| Risk Factor | High Risk Criteria |
|---|---|
| Alcohol (excessive) | Men >14 drink, Women >7 drinks per week |
| Blood pressure | Systolic >139 OR Diastolic >89 |
| Body weight | BMI ≥27.5 |
| Cholesterol | Total >239 OR LDL >160 |
| Existing medical condition | Heart, cancer, diabetes, stroke |
| HDL cholesterol | Men <35 or Women <45 |
| Illness days in past year | >5 |
| Life satisfaction | Partly or not satisfied |
| Perception of health | Fair or poor (on a 5-point scale) |
| Physical Activity | Less than one time per week |
| Safety belt usage | Less than 100% of the time |
| Smoking (tobacco) | Current smoker (user) |
| Stress | High (3-level scale: high, medium, low) |

TABLE 9

| Lifestyle Risk category | AHI Points |
|---|---|
| None - 0 risks | 100 |
| Low 1-2 risks | 75 |
| Medium 2-5 risks | 50 |
| High >5 risks | 25 |

H. Biometrics and Metabolic Syndrome

In one implementation, there may be five factors that are highly associated with the development of diabetes and vascular disease: (1) high blood pressure, (2) central obesity, (3) high triglycerides, (4) low HDL, and (5) elevated glucose. These biometric risk factors are shown in Table 10 with example criteria for high biometric risk.

TABLE 10

| Biometric Risks | High Biometric Risk Criteria |
|---|---|
| High Blood Pressure | BP ≥130/85 mmHg (SBP ≥130 or DBP ≥85) |
| Central Obesity | WC >40 in Men/WC >35 in Women or BMI ≥30 |
| High Triglycerides | TG ≥150 mg/dl |
| Low LDL Cholesterol | HDL <40 mg/dl in Men/HDL <50 mg/dl in Women |
| High Fasting Blood Sugar | Fasting Blood Sugar ≥100 mg/dl |

AHI point assignments for biometric risks are shown in Table 11, where the left column is a count of the number of biometric risks in Table 10 that satisfy the high biometric risk criteria.

TABLE 11

| Biometric Risks | AHI Points |
|---|---|
| 0 | 100 |
| 1 | 80 |
| 2 | 60 |
| 3 | 30 |
| 4 | 15 |
| 5 | 0 |

I. Socioeconomic Status

Socioeconomic status can be associated with health status. For this component, we use the zip code of a member's residence and the median household income for that residence to assign points for socioeconomic status. Given a member's zip code, the financial information can be obtained from the Internal Revenue Service Statistics of Income Division. The AHI points are assigned as follows in Table 12:

TABLE 12

| Income for Residence Zip Code | AHI Points |
|---|---|
| $0-$25k | 0 |
| $25k-$50k | 25 |
| $50k-$75k | 50 |
| $75k-$100k | 70 |
| $100k-$200k | 90 |
| >$200k | 100 |

J. Preventative Care

A member's participation in preventative care can be a component of their health status. Example preventative services are found in Table 13. AHI points can be assigned using Table 14 based on the counts of the number of preventative services that member participates in. In some implementations, the points may be assigned differently for males and females.

TABLE 13

| Preventative Services |
|---|
| Colorectal Screening |
| Breast cancer Screening |
| Cervical Cancer Screening |
| Dental check-up |
| PCP visit |
| Immunizations up to date |

TABLE 14

| Number of preventative Services | | AHI Points |
|---|---|---|
| Female | Male | |
| 4-6 | 4 | 100 |
| 3 | 3 | 75 |
| 2 | 2 | 50 |
| 1 | 1 | 25 |
| 0 | 0 | 0 |

K. Health Opportunities

Health opportunities are sometimes referred to as "gaps-in-care." These are a count of unresolved care considerations where a member is not complying with a recommended health action. The source of this data is the CareEngine. Unresolved care considerations represent non-compliance with evidence-based care and, therefore, are factors that influence health status. AHI points for unresolved health opportunities are show in table 15 below.

TABLE 15

| Number of Unresolved Health Opportunities | AHI Points |
|---|---|
| 0 | 100 |
| 1 | 80 |
| 2 | 60 |
| 3 | 30 |
| 4 | 15 |
| More than 4 | 0 |

L. Medication Adherence

The CareEngine® measures several markers of medication non-adherence as comorbidities. The Table 16 below assigns points based on the number of non-adherence markers a member has.

TABLE 16

| Number of Non-Adherence markers | AHI Points |
|---|---|
| 0 | 100 |
| 1 | 60 |
| 2 | 30 |
| 3 or more | 0 |

M. Behavioral Health Conditions

The CareEngine® measures several markers for the presence of behavioral health conditions. Because these conditions can have a significant impact on health and on the ability to improve health, they are considered independently. Example behavioral health conditions include:
  Autistic Disorder,
  Depression—Adult,
  Depression,
  Bipolar Disorder,
  Schizophrenia,
  Post-Traumatic Stress Disorder (PTSD), or
  Obsessive Compulsive Disorder.

In one example implementation, the behavioral health component is scored on a binary basis, where absence of a behavioral health condition gives 100 points, and presence of a behavioral health condition gives 0 points.

Methodology for Calculating the ActiveHealth Index

The preceding sections described example implementations for how a score is determined for each of the Active- Health Index components. An example of a set of component scores is shown below in Table 17 (in this example, component "M. Behavioral Health" is omitted). Each component may be given a weighting factor to weight the contribution that the component makes to the overall ActiveHealth Index. In some implementations, all the weights may be equal. The weights in Table 17 are illustrative. In some implementations, the weights can be determined via regression analysis to reflect the relative contribution of the components to overall health care spend and utilization.

TABLE 17

| Component | AHI Points | Weight | Weighted Points | Possible Points |
|---|---|---|---|---|
| A. Age/Gender | 80 | 0.7 | 56 | 70 |
| B. Self-Assessment | 100 | 0.5 | 50 | 50 |
| C. Minor Chronic | 60 | 0.4 | 24 | 40 |
| D. Major Chronic | 100 | 1 | 100 | 100 |
| E. Comorbidities | 75 | 0.5 | 37.5 | 50 |
| F. At Risk | 75 | 0.2 | 15 | 20 |
| G. Lifestyle Risks | 75 | 0.4 | 30 | 40 |
| H. Biometric Risks | 80 | 0.5 | 40 | 50 |
| I. Socioeconomic | 50 | 0.3 | 15 | 30 |
| J. Preventive Care | 75 | 0.4 | 30 | 40 |
| K. Health Opportunities | 100 | 0.4 | 40 | 40 |
| L. Medication Adherence | 100 | 0.4 | 40 | 40 |
| Total | | | 477.5 | 570 |

ActiveHealth Index: 477.7/570 = 83.8

In the example in Table 17, the data reflects a predominantly healthy 48 year old female who rates her health as excellent, has two minor chronic conditions, no major chronic conditions, one comorbidity, one at risk marker, 1-2 lifestyle risks, 1 biometric risk, lives in a middle class neighborhood, has had about half of the recommended preventative services, has no unresolved care considerations, and is on no medications for chronic conditions. This example member's AHI points are assigned using the Tables 1-16 above.

The member's weighted points are calculated by multiplying the assigned points by the weighting factors for the given component. The "Possible Points" column is calculated by multiplying the weight by the maximum score, e.g., 100, for each component.

To compute the member's ActiveHealth Index, the system divides the weighted point total by the possible point total. In this example, the ActiveHealth Index is computed as 477.7/570=83.8.

It is possible that the system may not have complete data necessary to calculate points for all components of the ActiveHealth Index. For example, if a member has not completed a health assessment questionnaire, then it is likely the system will not have the data to calculate the B. Self-Assessment or G. Lifestyle risk components. When points cannot be calculated for a component, the system may remove the particular component(s) from the analysis and redistribute the weights (e.g., in proportion to their original contributions) to calculate the ActiveHealth Index.

Each AHI component has a certain degree of impactability (or lack thereof). These are given in Table 18. The system may calculate an actual ActiveHealth Index for the member and an Optimal Index for a member. The Optimal Index is the score that could be achieved if all impactable components scored at 100 points (or whatever is the maximum possible points for a component). This is the total opportunity a member has to improve health. Table 18 shows the member's actual score on each component ("AHI points"), impactability factor and impactable points.

TABLE 18

| Component | AHI Points | Impactability Factor | Impactable Points |
|---|---|---|---|
| Age/Gender | 80 | 0 | 0 |
| Self-Assessment | 100 | 50 | 0 |
| Minor Chronic | 60 | 30 | 4.8 |
| Major Chronic | 100 | 0 | 0 |
| Comorbidities | 75 | 50 | 6.25 |
| At Risk | 75 | 50 | 2.5 |
| Lifestyle Risks | 75 | 80 | 8 |
| Biometric Risks | 80 | 100 | 10 |
| Socioeconomic | 50 | 10 | 1.5 |
| Preventive Care | 75 | 100 | 10 |
| Health Opportunities | 100 | 100 | 0 |
| Medication Adherence | 100 | 100 | 0 |
| Total | | | 43.05 |

Age and Gender are typically not impactable. The Self-assessment component is typically impactable, such that as health improves, risk factors are reduced and self-assessment of health should improve. With minor chronic conditions, many of these are acute illness and are impactable in that the marker may not be present on subsequent determinations. With major chronic conditions, these are largely permanent and not impactable in terms of their being present or not. With comorbidities and at-risk conditions, some are impactable while others are not, so the impactability score is intermediate for comorbidities and at-risk conditions. Lifestyle risks may be typically impactable, although medical conditions may not be. Biometric risks are impactable. The socioeconomic is minimally modifiable/impactable. Preventive care, health opportunities, and medication adherence are impactable.

Figure 4:
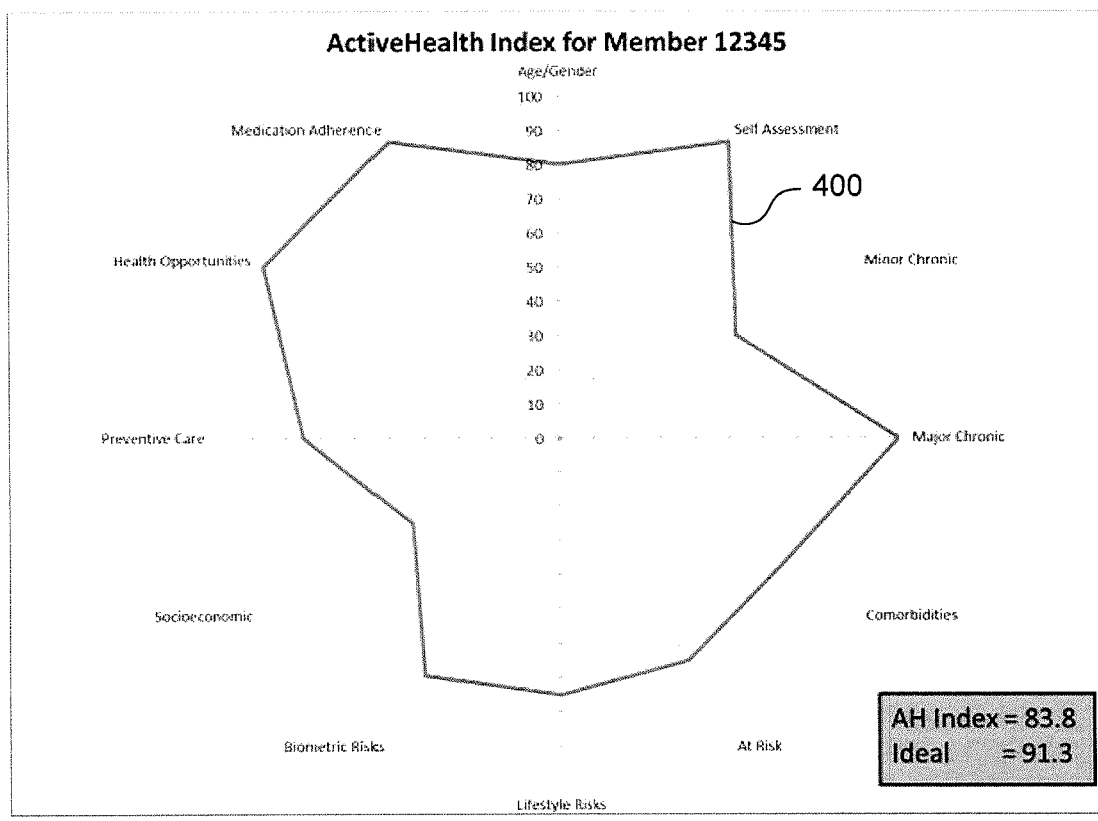
FIG. 4 is a diagram illustrating a member's actual health scoring and an optimal health scoring, according to one embodiment.

FIG. 4 is a diagram illustrating a member's actual health index and an optimal health index, according to one embodiment. The line 400 represents an individual's actual AHI score, where line segments connect the point value assigned to various components. This can be visualized in one implementation using such a "web" format as shown. Since some components are not impactable, the maximum value for those components may be equal to the current value, whereas for impactable components the maximum value may be greater than the current value.

Figure 5:
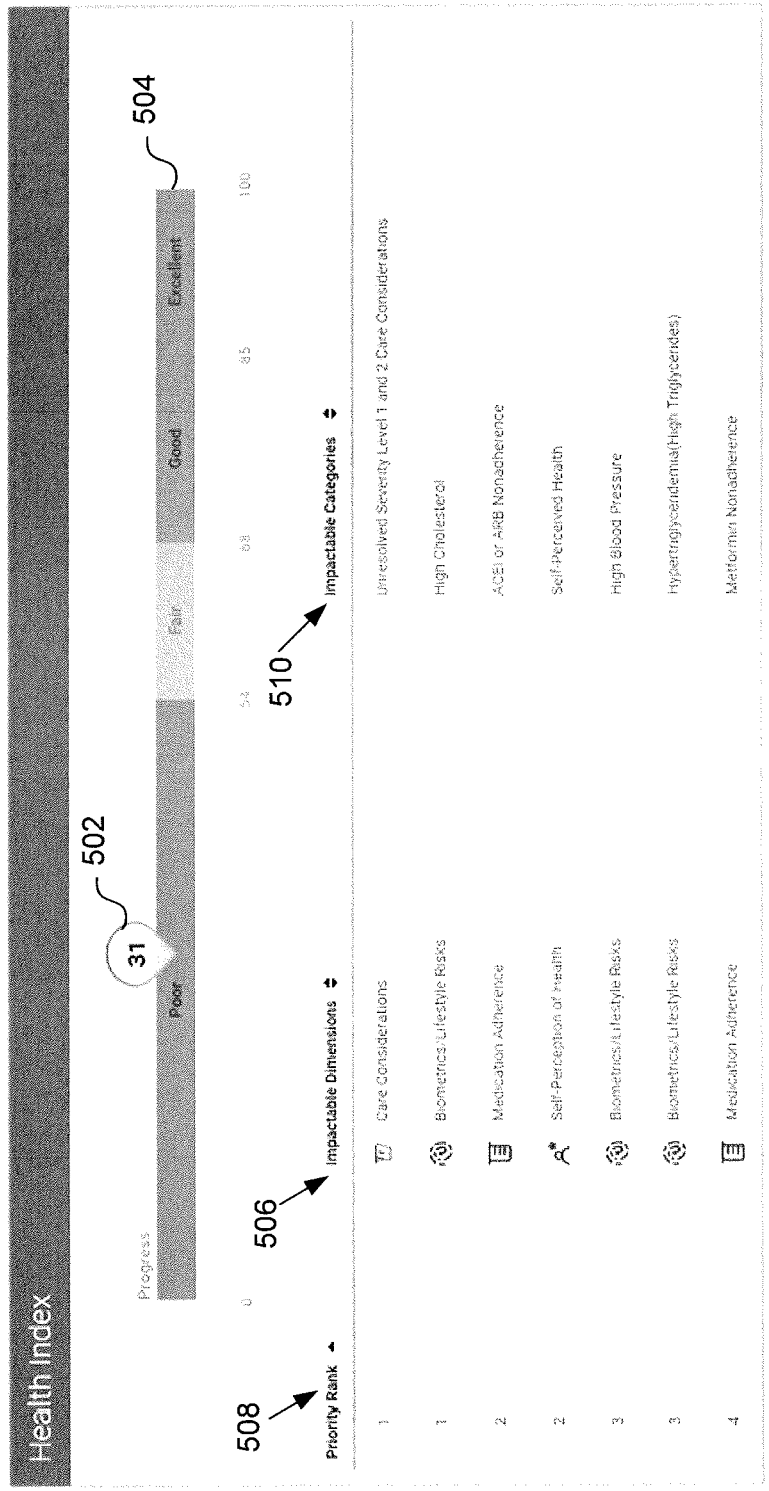
FIG. 5 is an example of a graphical user interface for displaying a health scoring and prioritized impactable components, according to one embodiment.

FIG. 5 is an example of a graphical user interface for displaying a health index and prioritized impactable components, according to one embodiment. A member's ActiveHealth Index, as described herein, is shown as icon 502. The icon 502 is shown relative to a range 504 of possible scores, for example 0 to 100. Impactable components 506 are shown in the graphical user interface with a corresponding priority rank 508. Additional information 510 is also provided for each impactable component 506. The priority rank 508 can be calculated to maximize clinical value and/or medical cost savings if the impactable category 506 is improved.

Financial Impact of Improving Health

In some implementations, a financial model can be executed to predict medical cost savings if certain impactable components are improved. In one implementation, the AHI can be computed for a given member using data from a particular time in the past, for example, two years ago. Then, the AHI can be computed for the given member using data from a second time, e.g., the present time or a more recent time in the past such as one year ago. The financial medical cost for the member is known for both time periods analyzed. In addition, any improvement in impactable components can be determined by comparing the values of the components between the two time periods analyzed. The improvement in impactable components can be correlated to financial savings for the given member. This same process can then be executed over a plurality of member and input into a financial model. Such a model would be able to identify which impactable variables correlate to financial savings (and how much financial savings) based on the amount of improvement in the impactable variable. The financial model can be used to provide members or health care providers with an estimate for lowered medical cost if certain impactable components are improves. This information can be used to help steer a member towards improving certain impactable components.

In one embodiment, a first financial model may be executed for chronic conditions, whereas a second financial model can be executed for non-chronic conditions. In some cases, chronic and non-chronic conditions are so medically different than the values for chronic patients and non-chronic patients can skew the results. As such, it may be more accurate in some cases to model chronic and non-chronic conditions separately.

Filtering Data Sources

Figure 6:
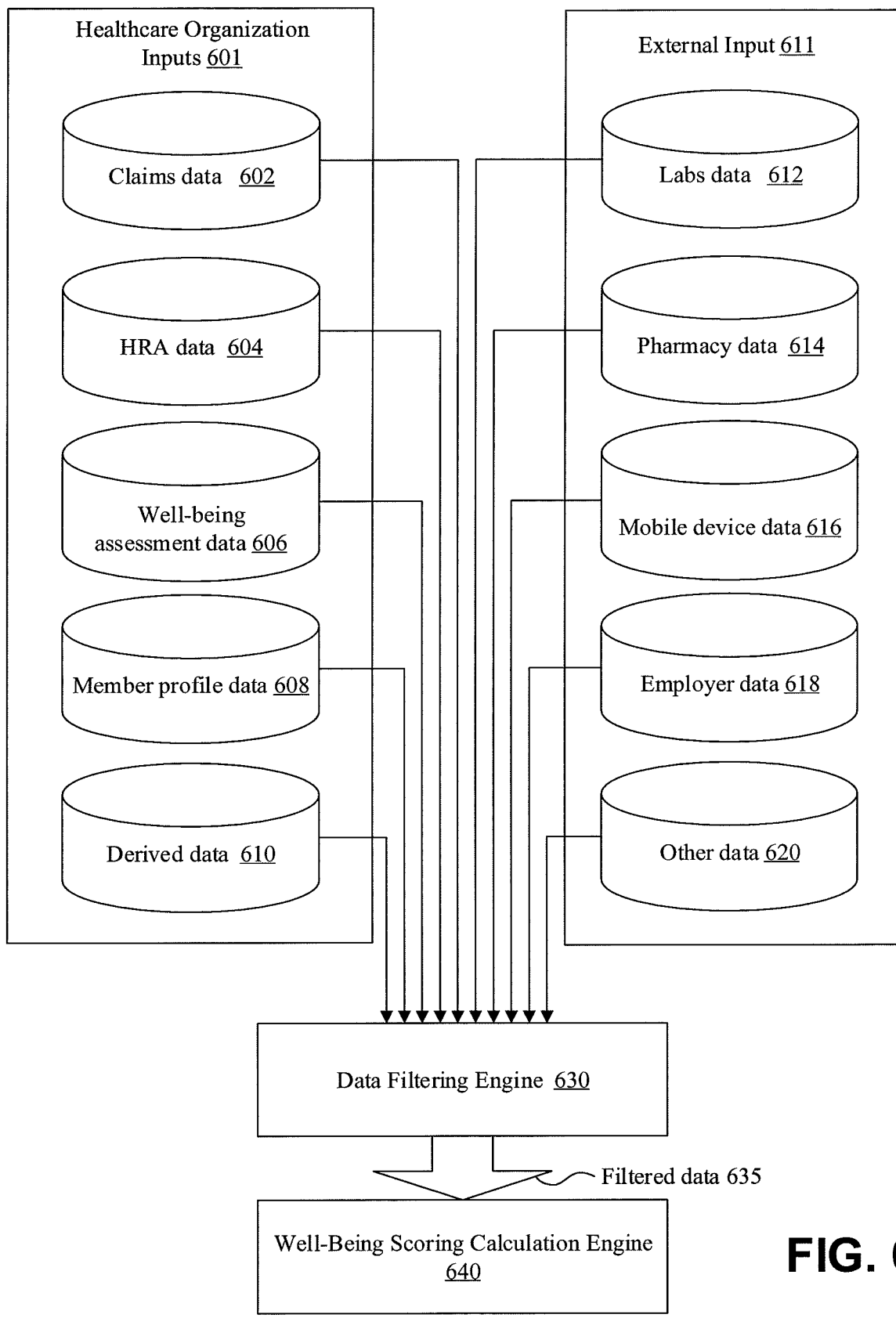
FIG. 6 is a block diagram illustrating data filtering in the context of generating a well-being scoring, according to one embodiment.

FIG. 6 is a block diagram illustrating data filtering in the context of generating a well-being scoring, according to one embodiment. A health care organization 100 computing device is configured to execute a data filtering engine 630 and a well-being calculation engine 640. The data filtering engine 630 and well-being calculation engine 640 may be embodied as software instructions stored in one or more memories and executed by one or more processors of the health care organization 100 computing device.

In order to generate the well-being scoring, various data sources are provided, including healthcare organization inputs 601 and external inputs 611. Healthcare organization inputs 601 include data sources that are available to the health care organization 100. Example healthcare organization inputs 601 include: claims data 602, HRA (health risk assessment) data 604, well-being assessment data 606, member profile data 608, and derived data 610. Healthcare organization inputs 601 also include other data, such as or electronic medical record (EMR) data. Claims data 602 comprises information about medical claims processed for a given member. HRA data 604 includes self-reported information relevant to a member's medical history and currently presented conditions. Well-being assessment data 606 includes responses to well-being assessment questions presented to the member. The well-being assessment questions may include questions directed to one or more dimensions of well-being, including but not limited to: (1) Physical Health, (2) Emotional Health, (3) Financial Security, (4) Social Connectedness, (5) Purpose, and (6) Character Strengths. Member profile data 608 includes personal identifying information about the member. Derived data 610 includes data that has been computed based on one or more of the claims data 602, HRA data 604, well-being assessment data 606, and member profile data 608. For example, derived data 610 may comprise categorized data of the member, such as an age group (e.g., 30-40 years old) that is based on a member's age. In some implementations, the derived data 610 combines two different pieces of data to categorize a member, such as age and obesity.

External inputs 611 are also used to generate the well-being scoring. External inputs 611 include data sources that are not available to the health care organization 100, and are provided by another source. Example external inputs 611 include laboratory data 612, pharmacy data 614, mobile device data 616, employer data 618, and other data 620. Laboratory data 612 includes lab test results from third party laboratories. Pharmacy data 614 includes prescription fulfillment data for the member. Mobile device data 616 includes data from a member's own personal devices, such as smart phones, smart watches and digital tracking devices. Example mobile device data 616 includes exercise data, activity data, sleep data, and other biometrics. Employer data 618 includes data about a member provided by the member's employer. Examples include demographic data, covered family member data, marital status, 401(k) participation, 401(k) contribution level, volunteer hours, career progression information, years on current job, use of vacation time, use of sick time, donation of personal time off (PTO), workers compensation use information, disability data, among others. Other data 620 may include any other data about the member, such as publicly available data from public databases or electronic medical record (EMR) data.

The healthcare organization inputs 601 (including the claims data 602, HRA data 604, well-being assessment data 606, member profile data 608, and derived data 610) and external inputs 611 (including the laboratory data 612, pharmacy data 614, mobile device data 616, employer data 618, and other data 620) are input to the data filtering engine 630. With a member database of a large number of members (e.g., over 1 million members) the amount of data in the healthcare organization inputs 601 and external inputs 611 is exceptionally large. If all of the healthcare organization inputs 601 and external inputs 611 were input into the well-being scoring calculation engine 640 directly, then a memory shortage could occur where there is not enough working memory to compute the well-being scoring. The memory shortage could exist for even a single member, and is exacerbated when the member database includes a large number of members (e.g., over 1 million members). Moreover, the amount of data to be copied from these data sources to compute the well-being scoring would be very large and would require an exceptionally large amount of storage.

As such, embodiments of the disclosure provide a data filtering engine 630 to filter the healthcare organization inputs 601 and external inputs 611 before providing filtered data 635 to the well-being calculation engine 640. In one implementation, each of the healthcare organization inputs 601 for a given member is associated with a unique individual identification number (IID). The IID is unique to the member and does not change if the member has two separate enrollments with the health care organization 100. For example, say that a member enrolls with the health care organization 100 with a first employer and is given a first member ID and an IID. If the member then switches employers (to a second employer) and enrolls again with the health care organization 100, the member will be provided a second member ID. However, the IID for the member enrolled with the second member ID remains the same as the IID assigned when the member was enrolled with the first member ID. The identity of the member being the same for the second enrollment (and thus providing for the same IID to be assigned to the member) can be based on analyzing certain member information, such as date of birth, name, and social security number.

The data filtering engine 630 receives data for a member from the various data sources in the healthcare organization inputs 601 and external inputs 611 and processes the data from each source separately. For example, the data filtering engine 630 may first receive the claims data 602. The data filtering engine 630 processes the claims to extract the IID from the claims data 602. Then the data filtering engine 630 copies the data used to calculate the well-being scoring from the claims data 602. In one implementation, a subset that is less that the complete set of claims data 602 is used by the well-being scoring calculation engine 640 to compute he well-being scoring. Other data that is not used by the well-being scoring calculation engine 640 to compute the well-being scoring is discarded by the data filtering engine 630. In the context of claims data 602, the not used information may include, for example, the names of the providers that provided the care associated with the various claims. In another implementation, the data can be filtered to copy only the most recent data. For example, if there are ten years of claims data for a member, only the recent data (e.g., recent 6 or 12 months) is copied. In this manner, the data filtering engine 630 minimizes the working memory needed to store the member data.

Also, in some embodiments, the data filtering engine 630 performs data type processing on the data that is not discarded. Performing data type processing can further minimize the size of the copied data and increase the computational efficiency of the copied data. The data filtering engine 630 assumes that any numerical data being copied is of a first data type, e.g., an integer. If the data being copied does not comply with the first data type (e.g., the number is not an integer, but rather includes a decimal), then the data is copied and assigned a second data type (e.g., floating point number). The first data type is a less complex data type than the second data type, where the first data type takes up less space (i.e., less bytes) of storage than the second data type. In this manner, by assuming that numbers can comply with the first data type when copying the data, and assigning the second data type in the situations where the data does not comply with the first data type, computation efficiency is improved by minimizing the amount of copied data.

The data filtering engine 630 then encrypts any sensitive personal information for the member to satisfy any compliance regulations, such as name, SSN, etc. The data filtering engine 630 then adds the data from the data source to an aggregate data structure (e.g., a table) for the member. In one implementation, a table structure can be used by the well-being scoring calculation engine 640, where each member is included in a separate row of the table. The data that is copied from the various healthcare organization inputs 601 and external inputs 611 is populated by the data filtering engine 630 into the columns of the table for the member. The well-being scoring calculation engine 640 can then compute the well-being scoring by computing scores for each of the six dimensions of well-being, and then aggregating the scores. To generate the scores for individual dimensions, the well-being scoring calculation engine 640 can pull whatever data is used for that dimension from the aggregate data structure of filtered data.

FIG. 7 is an example of a table 700 of filtered data 635 output by the data filtering engine 630 and used by the well-being scoring calculation engine 640 to compute the well-being scoring, according to one embodiment. The table 700 includes rows 702 and columns 704. Each row 702 represents a different member. The columns 704 include an IID (individual identifier) for each member and data columns, e.g., data columns 710, 720. Data columns 710 include the filtered data from a first data source (e.g., one of the healthcare organization inputs 601 and external inputs 611) and data columns 720 include the filtered data from a second data source (e.g., a different one of the healthcare organization inputs 601 and external inputs 611). Additional data columns can be included for each set of filtered data from each one of the healthcare organization inputs 601 and external inputs 611.

Figure 8:
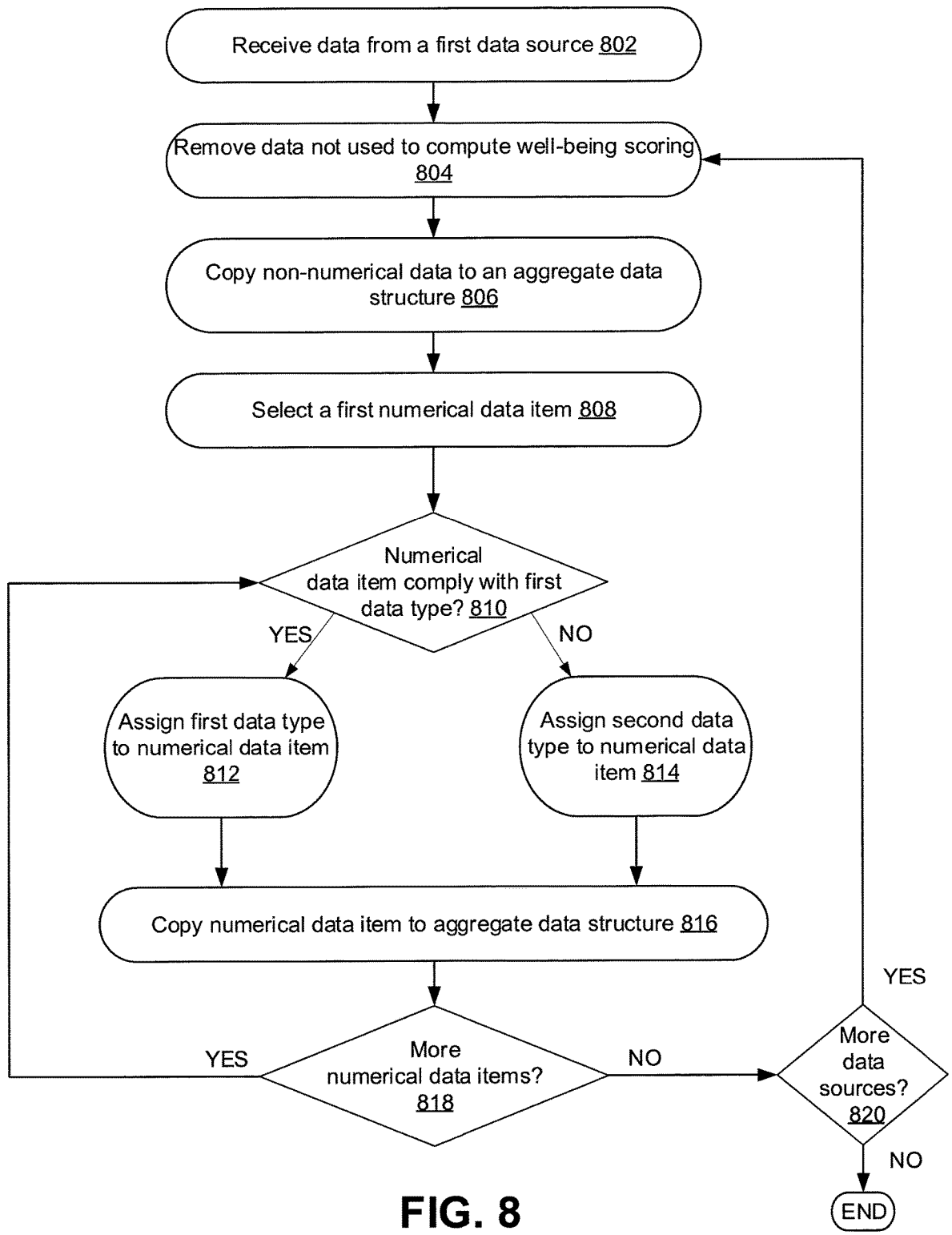
FIG. 8 is a flow diagram illustrating filtering data to minimize computational resources when computing a well-being scoring, in accordance with one embodiment.

FIG. 8 is a flow diagram illustrating filtering data to minimize computational resources when computing a well-being scoring, in accordance with one embodiment. The method in FIG. 8 may be executed by a processor associated with a heath care organization 100 computing device executing instructions stored in a memory.

At step 802, the processor receives data from a first data source. The first data source may be any of the healthcare organization inputs 601 and external inputs 611 shown in FIG. 6. At step 804, the processor removes data not used to compute well-being scoring. For example, certain data is simply not used to compute well-being scoring, such as data that falls outside a certain date range (e.g., within past 12 months). Other data, such as provider name, provider phone number, etc. are simply not relevant to computing well-being scoring and can also be removed.

At step 806, the processor copies the non-numerical data that passes step 804 to an aggregate data structure. The aggregate data structure may be a table, such as the table shown in FIG. 7.

At step 808, the processor selects a first numerical data item. At step 810, the processor determines whether the numerical data item complies with a first data type. For example, the first data type may be a 1-byte integer (e.g., TINYINT), 2-byte integer (e.g., SMALLINT), or 4-byte integer (e.g., INT) data type. If at step 810 the processor determines that the numerical data item does comply with the first data type, then the method proceeds to step 812, where the processor assigns the first data type to the numerical data item, and at step 816 copies the numerical data item (assigned the first data type) to the aggregate data structure.

If at step 810 the processor determines that the numerical data item does not comply with the first data type, then the method proceeds to step 814, where the processor assigns a second data type to the numerical data item, and at step 816 copies the numerical data item (assigned the second data type) to the aggregate data structure. The second data type is more complex and take up more storage space than the first data type. For example, the second data type could be 4-btye number (e.g., FLOAT (floating point number)) or an 8-byte number (e.g., DOUBLE (double-precision floating point number)).

At step 818, the processor determines whether any more numerical data items are left to be processed for the data source. If yes, the method returns to step 810. In this manner the processor assigns the smaller memory-wise first data type to any numerical data items that can accept such a data type, and relies on the larger memory-wise second data type for any numerical data items that cannot accept such the first data type. As such, computer-readable storage space is minimized in the aggregate data structure.

If that step 818, the processor determines that there are not any more numerical data items are left to be processed for the data source, then the method proceeds to step 820, where the processor determines whether there are any additional data sources (e.g., from the healthcare organization inputs 601 and external inputs 611) left to process. If yes, the method returns to step 804. If not, the method ends, and the aggregate data structure is ready to be processed by the well-being calculation engine 640 to compute the well-being scoring.

It should be noted that the method for minimizing computational resources when copying data of FIG. 8 can be used to create an aggregate data structure used to perform any computation corresponding to the member, and is not limited to a well-being scoring. For example, the method for minimizing computational resources when copying data of FIG. 8 can be used to create an aggregate data structure used to compute a health index for a member. The method for minimizing computational resources when copying data of FIG. 8 can also be used to create an aggregate data structure used to execute any analytical model corresponding to the member and data corresponding to the member.

For situations in which the systems discussed here collect personal information about users, or may make use of personal information, the users may be provided with an opportunity to control whether programs or features collect the personal information (e.g., information about a user's social network, social actions or activities, profession, a user's preferences, or a user's current location, medical information, date of birth, contact information, financial information, etc.), or to control whether and/or how to retrieve content from a server. In addition, certain data may be anonymized in one or more ways before it is stored or used, so that personally identifiable information is removed. For example, a user's identity may be anonymized so that no personally identifiable information can be determined for the user, or a user's geographic location may be generalized where location information is obtained (such as, for example, to a city, ZIP code, or state level), so that a particular location of a user cannot be determined. Thus, the user may have control over how information is collected about him or her and used by the systems discussed herein.

All references, including publications, patent applications and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method for minimizing computational resources when copying data, the method comprising:
   receiving, by a processor, a first set of data from a first data source, wherein the first set of data includes a portion of data used to compute a well-being scoring for a member and a portion of data not used to compute the well-being scoring for the member;
   copying, by the processor, non-numerical data items included in the portion of the data from the first set of data used to compute the well-being scoring to an aggregate data structure; and
   for each numerical data item in the portion of the data from the first set of data used to compute the well-being scoring:
      assigning, by the processor, a first data type to the numerical data item if the numerical item complies with the first data type and assigning, by the processor, a second data type to the numerical data item if the numerical item does not comply with the first data type, wherein the first data type uses less bytes than the second data type to store the numerical data item, and
      copying, by the processor, the numerical data item having the assigned first or second data type to the aggregate data structure, wherein the well-being scoring is calculated for the member based on the aggregate data structure, wherein the well-being scoring comprises a plurality of dimensions, wherein each dimension in the plurality of dimensions comprises a score for the dimension that is computed based on data in the aggregate data structure.

2. The method of claim 1, wherein the first data type is an integer data type and the second data type is a floating point number data type.

3. The method of claim 1, wherein:
   the first data type uses 1 byte to store the numerical data item, and the second data type uses 2 bytes to store the numerical data item; or
   the first data type uses 1 byte to store the numerical data item, and the second data type uses 4 bytes to store the numerical data item; or
   the first data type uses 1 byte to store the numerical data item, and the second data type uses 8 bytes to store the numerical data item; or
   the first data type uses 2 bytes to store the numerical data item, and the second data type uses 4 bytes to store the numerical data item; or
   the first data type uses 2 bytes to store the numerical data item, and the second data type uses 8 bytes to store the numerical data item; or
   the first data type uses 4 bytes to store the numerical data item, and the second data type uses 8 bytes to store the numerical data item.

4. The method of claim 1, wherein the aggregate data structure comprises a table, where each row of the table comprises a different member, and each column comprises data used to compute the well-being scoring for the different members.

5. The method of claim 1, further comprising:
displaying the well-being scoring in a graphical user interface, wherein the scores for each dimension in the plurality of dimensions are displayed in the graphical user interface.

6. The method of claim 1, wherein each dimension of the plurality of dimensions contributes equally to the well-being scoring.

7. The method of claim 1, wherein each dimension of the plurality of dimensions respectively corresponds to weight value for the dimension, wherein the weight values represent how much each dimension contributes to the well-being scoring.

8. The method of claim 1, wherein for a first dimension of the plurality of dimensions, a plurality of data items contribute to a first score for the first dimension.

9. The method of claim 8, wherein each data item of the plurality of data items respectively corresponds to weight value for the data item, wherein the weight values represent how much each data item contributes to the first score for the first dimension.

10. The method of claim 1, wherein the first set of data from the first data source includes data corresponding to answers to assessment questions answered by the member.

11. The method of claim 1, further comprising:
receiving a second set of data from a second data source, wherein the second set of data includes a portion of data used to compute the well-being scoring for the member and a portion of data not used to compute the well-being scoring for the member;
copying non-numerical data items included in the portion of the data from the second set of data used to compute the well-being scoring to the aggregate data structure; and
for each numerical data item in the portion of the data from the second set of data used to compute the well-being scoring: assigning the first data type to the numerical data item if the numerical item complies with the first data type and assigning the second data type to the numerical data item if the numerical item does not comply with the first data type, and copying the numerical data item having the assigned first or second data type to the aggregate data structure.

12. The method of claim 1, wherein the first data source comprises one or more of a claims data, assessment questionnaire answer data, member profile data, laboratory data, pharmacy data, mobile device data, electronic medical record (EMR) data, or employer data.

13. A computer system, comprising:
a memory storing instructions; and
a processor for executing the instructions to cause the computer system to:
  receive a first set of data from a first data source, wherein the first set of data includes a portion of data used to compute a well-being scoring for a member and a portion of data not used to compute the well-being scoring for the member;
  copy non-numerical data items included in the portion of the data from the first set of data used to compute the well-being scoring to an aggregate data structure;
  for each numerical data item in the portion of the data from the first set of data used to compute the well-being scoring: assign a first data type to the numerical data item if the numerical item complies with the first data type and assign a second data type to the numerical data item if the numerical item does not comply with the first data type, wherein the first data type uses less bytes than the second data type to store the numerical data item, and copy the numerical data item having the assigned first or second data type to the aggregate data structure; and
  generate the well-being scoring for the member based on the aggregate data structure, wherein the well-being scoring comprises a plurality of dimensions, wherein each dimension in the plurality of dimensions comprises a score for the dimension that is computed based on data in the aggregate data structure.

14. The computer system of claim 13, wherein:
the first data type uses 1 byte to store the numerical data item, and the second data type uses 2 bytes to store the numerical data item; or
the first data type uses 1 byte to store the numerical data item, and the second data type uses 4 bytes to store the numerical data item; or
the first data type uses 1 byte to store the numerical data item, and the second data type uses 8 bytes to store the numerical data item; or
the first data type uses 2 bytes to store the numerical data item, and the second data type uses 4 bytes to store the numerical data item; or
the first data type uses 2 bytes to store the numerical data item, and the second data type uses 8 bytes to store the numerical data item; or
the first data type uses 4 bytes to store the numerical data item, and the second data type uses 8 bytes to store the numerical data item.

15. The computer system of claim 13, wherein each dimension of the plurality of dimensions respectively corresponds to weight value for the dimension, wherein the weight values represent how much each dimension contributes to the well-being scoring.

16. The computer system of claim 13, wherein the first set of data from the first data source includes data corresponding to answers to assessment questions answered by the member.

17. A non-transitory computer-readable storage medium storing instructions that, when executed by a processor, cause the processor to minimize computational resources when copying data, by performing the steps of:
receiving a first set of data from a first data source, wherein the first set of data includes a portion of data used to compute a well-being scoring for a member and a portion of data not used to compute the well-being scoring for the member;
copying non-numerical data items included in the portion of the data from the first set of data used to compute the well-being scoring to an aggregate data structure; and
for each numerical data item in the portion of the data from the first set of data used to compute the well-being scoring:
  assigning a first data type to the numerical data item if the numerical item complies with the first data type and assigning a second data type to the numerical data item if the numerical item does not comply with the first data type, wherein the first data type uses less bytes than the second data type to store the numerical data item, and
  copying the numerical data item having the assigned first or second data type to the aggregate data structure, wherein the well-being scoring is calculated for the member based on the aggregate data structure, wherein the well-being scoring comprises a plurality of dimensions, wherein each dimension in the plurality of dimensions comprises a score for the dimension that is computed based on data in the aggregate data structure.

18. The computer-readable storage medium of claim 17, wherein:
the first data type uses 1 byte to store the numerical data item, and the second data type uses 2 bytes to store the numerical data item; or
the first data type uses 1 byte to store the numerical data item, and the second data type uses 4 bytes to store the numerical data item; or
the first data type uses 1 byte to store the numerical data item, and the second data type uses 8 bytes to store the numerical data item; or
the first data type uses 2 bytes to store the numerical data item, and the second data type uses 4 bytes to store the numerical data item; or
the first data type uses 2 bytes to store the numerical data item, and the second data type uses 8 bytes to store the numerical data item; or
the first data type uses 4 bytes to store the numerical data item, and the second data type uses 8 bytes to store the numerical data item.

* * * * *